United States Patent [19]

Kumar et al.

[11] Patent Number: 5,488,055
[45] Date of Patent: Jan. 30, 1996

[54] SUBSTITUTED N-CYCLOALKYLMETHYL-1H-PYRAZOLO (3,4-B)QUINOLIN-4 AMINES AND COMPOSITIONS AND METHODS OF USE THEREOF

[75] Inventors: Virendra Kumar, Paoli, Pa.; John A. Dority, Jr., West Haven, Conn.

[73] Assignee: Sanofi Winthrop Inc., New York, N.Y.

[21] Appl. No.: 402,269

[22] Filed: Mar. 10, 1995

[51] Int. Cl.⁶ .................. C07D 471/04; A61K 31/47
[52] U.S. Cl. .................. 514/293; 514/232.8; 544/126; 546/82
[58] Field of Search ................ 544/126; 546/82; 514/232.8, 293

[56] References Cited

U.S. PATENT DOCUMENTS 4,013,665  3/1977  Crenshaw et al. .................. 546/82

OTHER PUBLICATIONS

Stein et al, J. Med. Chem. 1970, 13(10), 153–155.
Zikan et al, Chem. Abstracts 108:204613K (1988).
Zikan et al, Chem. Abstracts 106:138447q (1987).
Radl et al, Chem. Abstracts 106:18429P (1987).
Radl et al, Chem. Abstracts 105:226434T (1986).
Crenshaw et al, J. Med. Chem., 1976, 19(2), 262–275.

Primary Examiner—Mukund J. Shah
Assistant Examiner—Philip I. Datlow
Attorney, Agent, or Firm—Paul E. Dupont

[57] ABSTRACT

Substituted N-cycloalkylmethyl-1H-pyrazolo[3,4-b] quinolin-4-amines, pharmaceutical compositions containing them and methods for a) effecting c-GMP-phosphodiesterase inhibition, b) treating heart failure and/or hypertension, c) reversing or reducing nitrate-induced tolerance and d) treating angina pectoris, congestive heart disease and myocardial infarction utilizing them.

54 Claims, No Drawings

SUBSTITUTED N-CYCLOALKYLMETHYL-1H-PYRAZOLO (3,4-B)QUINOLIN-4 AMINES AND COMPOSITIONS AND METHODS OF USE THEREOF

BACKGROUND OF THE INVENTION (a) Field of the Invention

The invention relates to substituted N-cycloalkylmethyl-1H-pyrazolo[3,4-b]quinolin-4-amines, to pharmaceutical compositions containing them and to methods for a) effecting c-GMP-phosphodiesterase inhibition, b) treating heart failure and/or hypertension, c) reversing or reducing nitrate-induced tolerance and d) treating angina pectoris, congestive heart disease and myocardial infarction utilizing them.

(b) Information Disclosure Statement

Crenshaw et al., J. Med. Chem. 1976, 19 (2), 262–275, disclose a series of N-substituted-1,3-dimethyl-1H-pyrazolo [3,4-b]quinolin- 4-amines which are said to be useful as interferon inducing agents. Specifically disclosed are N-cyclopropyl, N-tricyclo[ 3.3.1.13,7]dec-1-yl, N-(3-pyridinylmethyl), and N-[[2-(dimethylamino) phenyl]methyl]-1,3-dimethyl-1H-pyrazolo[3,4-b]quinolin- 4-amines, as well as N-(1,3-dimethyl-1H-pyrazolo[3,4-b]quinolin- 4-yl)-N'-tricyclo[3.3.1.1$^{3.7}$]dec-1-yl-1,3-propane diamine which were found to be inactive in the interferon assay. Similar derivatives are disclosed in U.S. Pat. No. 4,013,665, issued March 22, 1977.

Stein et al., J. Med. Chem. 1970, 13 (1), 153–155, disclose a series 4-lower-alkylamino and 4-phenylamino-1,3-dimethyl- 1H-pyrazolo[3,4-b]quinolines which were tested and found to exhibit no appreciable antimalarial activity.

Zikan et al., Chemical Abstracts 108:204613K, disclose 4-carboxyalkylamino-1,3-dimethyl-1H-pyrazolo[3,4-b] quinolines which are said to be useful as antiviral agents.

Zikan et al. Chemical Abstracts 106:138447q disclose a series of substituted 4-anilino-1,3-dimethyl-1H-pyrazolo[3,4-b]quinolines which are said to be useful as antiviral agents.

Radl et al., Chemical Abstracts 106:18429P, disclose a series of 1-substituted-4-(N-substituted amino)-3-methyl-1H-pyrazolo[ 3, 4-b]quinolines which are said to be useful as potential antiviral agents. Specifically disclosed are N-[(4-methoxyphenyl) methyl], N-(phenylmethyl), N-(2-phenylethyl) and N-cyclohexyl- 1,3-dimethyl- 1H-pyrazolo [3,4-b]quinolin- 4-amines. Radl et al., Chemical Abstracts 105:226434T, disclose a series of 4-hydroxyanilino and 4-alkoxyanilino-1,3-dimethyl-1-H-pyrazolo[ 3,4-b]quinolines which are said to be useful as potential antiviral agents.

SUMMARY OF THE INVENTION

The invention relates to compounds of the Formula I:

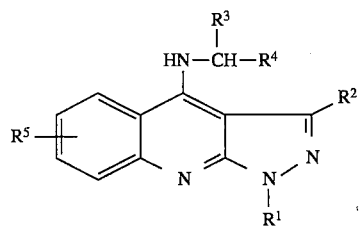

wherein:

$R^1$ is lower-alkyl, phenyl-lower-alkyl, or cycloalkyl;

$R^2$ is hydrogen, or lower-alkyl;

$R^3$ is hydrogen, lower-alkyl, or hydroxylower-alkyl;

$R^4$ is cycloalkyl or cylcoalkyl substituted by from one to two, the same or different, substituents selected from the group consisting of lower-alkoxycarbonyl, carboxy, lower-alkylthio-lower-alkoxycarbonyl, hydroxylower-alkyl, hydroxy, oxo, lower-alkoxy, lower-alkyl, and halogen; and $R^5$ is from one to three, the same or different, substituents selected from the group consisting of hydrogen, lower-alkoxy, hydroxy, dilower-alkylamino-lower-alkoxy, carboxylower-alkoxy, lower-alkoxycarbonyl-lower-alkoxy, nitro, polyhydroxylower-alkoxy, amino, epoxylower-alkoxy, carboxy, lower-alkanoylamino, lower-alkoxycarbonyl, pyridinyl, 4-morpholinyl-lower-alkoxy, lower-alkylsulfonyl, cyano, 1-imidazolyl, halogen, dilower-alkylaminosulfonyl, oxadiazolyl (or oxadiazolyl substituted on any available carbon atom thereof by lower-alkyl), lower-alkylsulfinyl, 1-pyrazolyl (or 1-pyrazolyl substituted on any available carbon atom thereof by lower-alkyl), trifluoromethylsulfonyl, lower-alkenyl, lower-alkyl, and lower-alkynyl; or a pharmaceutically acceptable acid-addition salt and/or hydrate and/or solvate thereof, or, where applicable, a stereoisomer or a racemic mixture thereof.

The compounds of the Formula I have been found to possess c-GmP-PDE V inhibitory activity and are thus useful in the treatment of heart failure and/or hypertension. The compounds of the Formula I, in combination with nitrates, have also been found to be useful for reversing or reducing nitrate-induced tolerance and thus would be further useful in the treatment of angina pectoris, congestive heart disease and myocardial infarction.

Preferred compounds of Formula I above are those wherein:

$R^1$, $R^2$ and $R^3$ are as defined hereinabove;

$R^4$ is cycloalkyl or cylcoalkyl substituted by one substituent selected from the group consisting of lower-alkoxycarbonyl, lower-alkylthio-lower-alkoxycarbonyl, hydroxylower-alkyl, hydroxy, and oxo; and $R^5$ is from one to two, the same or different, substituents selected from the group consisting of hydrogen, lower-alkoxy, hydroxy, dilower-alkylamino-lower-alkoxy, carboxylower-alkoxy, nitro, polyhydroxylower-alkoxy, amino, epoxylower-alkoxy, carboxy, lower-alkanoylamino, lower-alkoxycarbonyl, pyridinyl, 4-morpholinyl-lower-alkoxy, lower-alkylsulfonyl, cyano, 1-imidazolyl, halogen, dilower-alkylaminosulfonyl, oxadiazolyl substituted on any available carbon atom thereof by lower-alkyl, lower-alkylsulfinyl, 1-pyrazolyl (or 1-pyrazolyl substituted on any available carbon atom thereof by lower-alkyl), trifluoromethylsulfonyl, and lower-alkenyl.

Particularly preferred compounds of Formula I above are those wherein:

$R^1$ is ethyl, isopropyl, benzyl, or cyclopentyl; and $R^2$ is hydrogen, or methyl; $R^3$ is hydrogen, methyl, ethyl, or hydroxymethyl; and $R^4$ and $R^5$ are as defined directly above.

The most preferred compounds of the Formula I above are those wherein:

$R^1$ is ethyl, isopropyl, benzyl, or cyclopentyl;

$R^2$ is hydrogen, or methyl; $R^3$is hydrogen, methyl, ethyl, or hydroxymethyl;

$R^4$ is cycloalkyl selected from the group consisting of cyclohexyl, cyclopropyl, and adamantyl or said cycloalkyl group substituted by one substituent selected from the group consisting of methoxycarbonyl, methylthiomethoxycarbonyl, hydroxymethyl, hydroxy, and oxo; and $R^5$ is from one to two, the same or different, substituents selected from the group consisting of hydrogen, methoxy, hydroxy, 2-(dimethylamino) ethoxy, carboxymethoxy, nitro, 2,3-dihydroxypropoxy, amino, 2,3-epoxypropoxy, 1-carboxyethoxy, carboxy, acetylamino, methoxycarbonyl, pyridinyl, 2-(4-morpholinyl) ethoxy, methylsulfonyl, cyano, 1-imidazolyl, bromo, diethylaminosulfonyl, 5-methyl-3-(1,2,4-oxadiazolyl), methylsulfinyl, 4-methyl-1-pyrazolyl, 1-pyrazolyl, trifluoromethylsulfonyl, and ethenyl; for example, 1-ethyl-6-nitro-N-[S(+)-1-(cyclohexyl)ethyl]-1H-pyrazolo [3,4-b]quinolin-4-amine.

The invention further relates to pharmaceutical compositions which comprise compounds of Formula I together with a pharmaceutically acceptable carrier, adjuvant, diluent, or vehicle.

The invention further relates to a method for effecting cGMP-phosphodiesterase inhibition in a mammalian organism which comprises administering to said organism an effective amount of a compound of Formula I.

The invention further relates to a method for treating heart failure and/or hypertension in a mammalian organism which comprises administering to said organism an effective amount of a compound of the Formula I.

The invention further relates to a method for reversing or reducing nitrate-induced tolerance in a mammalian organism undergoing nitrate therapy which comprises administering to said organism an effective amount of a compound of the Formula I.

The invention further relates to a method for treating angina pectoris, congestive heart disease and myocardial infarction in a mammalian organism which comprises administering to said organism an effective amount of a compound of the Formula I in combination with a nitrate.

DETAILED DESCRIPTION INCLUSIVE OF PREFERRED EMBODIMENTS

The term lower-alkyl as used herein means linear or branched hydrocarbon chains having from one to about four carbon atoms and thus includes methyl, ethyl, propyl, isopropyl, n-butyl, sec-butyl, and the like.

The term lower-alkoxy as used herein means linear or branched alkyloxy substituents having from one to about four carbon atoms and thus includes methoxy, ethoxy, propoxy, isopropoxy, butoxy, sec-butoxy, and the like.

The term halogen, halide, or halo as used herein means bromine, chlorine, iodine or fluorine.

The term lower-alkenyl as used herein means branched or unbranched unsaturated hydrocarbon radicals of from two to about four carbon atoms and thus includes 1-ethenyl, 1-propenyl, 2-propenyl, 1-methyl-2-propenyl, isopropenyl, 2-butenyl, isobutenyl, and the like.

The term cycloalkyl as used herein means bridged or unbridged hydrocarbon ring systems having from three to about 10 carbon atoms and thus includes cyclopropyl, cyclobutyl, cyclopentyl, cyclohexyl, cycloheptyl, cyclooctyl, cyclodecyl, norbornyl, adamantyl, and the like.

The term polyhydroxylower-alkoxy as used herein means lower-alkoxy as defined above which is substituted by from two to about four hydroxy groups none of which are attached to the $C_1$ carbon atom and thus includes 2,3-dihydroxypropoxy, 3,4-dihydroxybutoxy, and the like.

The term epoxylower-alkoxy as used herein means lower-alkoxy as defined above in which the lower-alkoxy group also contains an epoxy group which is bonded to other than the $C_1$ carbon atom and thus includes 2,3-epoxypropoxy, 3,4-epoxybutoxy, and the like.

The term lower-alkanoyl as used herein means linear or branched hydrocarbon chains having two to about four carbon atoms and thus includes acetyl, propionyl, butyryl, isobutyryl, and the like.

The term lower-alkynyl as used herein means branched or unbranched unsaturated hydrocarbon radicals of from two to about four carbon atoms and thus includes 1-ethynyl, 1-propynyl, 2-propynyl, 2-butynyl, 1-methyl-2-propynyl, and the like.

The synthesis of compounds of the invention may be outlined as shown in Scheme A:

Scheme A

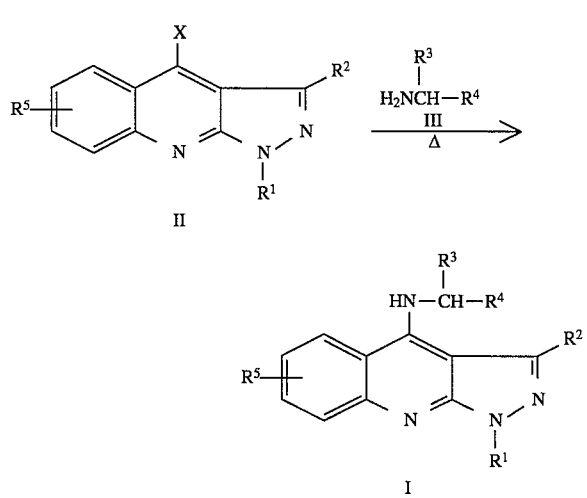

A suitably substituted 4-halo-1H-pyrazolo[3,4-b]quinoline of the formula II, wherein X is a halogen, preferably chlorine, in a suitable organic solvent, such as dimethylsulfoxide, is treated with at least one mole of a suitably substituted amine of the formula III, optionally in the presence of at least one mole of a suitable base, such as triethylamine, at a temperature in the range of about room temperature up to the boiling point of the solvent used, preferably at a temperature in the range of about 80° C. up to the boiling point of the solvent used, to afford the substituted 1H-pyrazolo[3,4-b]quinolin-4-amines of the formula I.

Simple chemical transformations which are conventional and well known to those skilled in the art of chemistry can be used for effecting changes in the functional groups of the compounds of the formula I. For example, treatment of acids with reducing agents, e.g. LAH, to afford the corresponding alcohols, the dealkylation of aryl ethers to afford the corresponding phenol derivatives, treatment of phenol derivatives with alkylating agents to afford the corresponding ether derivatives, the acid catalyzed ring opening of epoxides to afford the corresponding diols, the catalytic reduction of nitro derivatives to afford the corresponding amines, oxidation of alcohols to afford the corresponding oxo derivatives, the treatment of aryl halides with carbon monoxide in the presence of a suitable lower-alkanol and a suitable catalyst, e.g. $Pd(Ph_3)_2Cl_2$, to afford the corresponding lower-alkoxycarbonyl substituted aryl derivatives, the hydrolysis of esters to afford the corresponding acid derivatives, the treatment of aryl halides with CuCN or a mixture of CuCN/NaCN to afford the corresponding nitrile derivatives, the treatment of nitriles with hydroxylamine hydrochloride to afford the corresponding oxime derivatives, the treatment of aryl halides with nucleophilic aromatic heterocycles, such as pyrazole and imidazole derivatives, to afford the corresponding aromatic heterocycle substituted aryl derivatives, and the treatment of aryl halides with (lower-alkenyl)Sn-(lower-alkyl)$_3$ derivatives in the presence of a suitable catalyst, e.g. Pd(Ph$_3$)$_2$Cl$_2$, to afford the corresponding lower-alkenyl substituted aryl derivatives.

It will be appreciated that the compounds of the Formula I can possess one or more asymmetric carbon atoms and are thus capable of existing in a number of stereoisomeric forms, i.e. enantiomers and diastereomers. Unless otherwise specified herein, the invention is intended to extend to each of these stereoisomeric forms and to mixtures thereof, including the racemates. In some cases there may be advantages, i.e. greater potency, to using a particular enantiomer when compared to the other enantiomer or the racemate in the methods of the instant invention and such advantages can be readily determined by those skilled in the art. The separate enantiomers may be synthesized from chiral starting materials or the racemates may be resolved by conventional procedures which are well known in the art of chemistry such as chiral chromatography, fractional crystallization of diastereomeric salts and the like. Likewise, the diastereomers can be separated by conventional procedures which are well known in the art of chemistry such as chromatography, fractional crystallization and the like.

The compounds of Formula I are useful both in the free base form and in the form of acid-addition salts, and, both forms are within the purview of the invention. The acid-addition salts are often a more convenient form for use; and in practice, use of the salt form inherently amounts to use of the base form. The acids which can be used to prepare the acid-addition salts include preferably those which produce, when combined with the free base, pharmaceutically-acceptable salts, that is, salts whose anions are relatively innocuous to the animal organism in pharmaceutical doses of the salts, so that the beneficial properties inherent in the free base are not vitiated by side effects ascribable to the anions. In practicing the present invention it is convenient to use the free base form or the hydrochloride, fumarate, toluenesulfonate, methanesulfonate or maleate salts. However, other appropriate pharmaceutically acceptable salts within the scope of the invention are those derived from other mineral acids and organic acids. The acid-addition salts of the basic compounds are prepared by standard procedures well known in the art which include, but are not limited thereto, dissolving the free base in an aqueous alcohol solution containing the appropriate acid and isolating the salt by evaporating the solution, or by reacting the free base and an acid in an organic solvent, in which case the salt separates directly, or is precipitated with a second organic solvent, or can be obtained by concentration of the solution. Although medicinally acceptable salts of the basic compounds are preferred, all acid-addition salts are within the scope of the present invention. All acid-addition salts are useful as sources of the free base form even if the particular salt per se is desired only as an intermediate product, as, for example, when the salt is formed for purposes of purification or identification, or when it is used as an intermediate in preparing a medicinally acceptable salt by, for example, ion exchange procedures.

The suitably substituted 4-halo-1H-pyrazolo[3,4-b]quinolines of the formula II, which are required for the synthesis of the compounds of the formula I, can be prepared as shown in Scheme B:

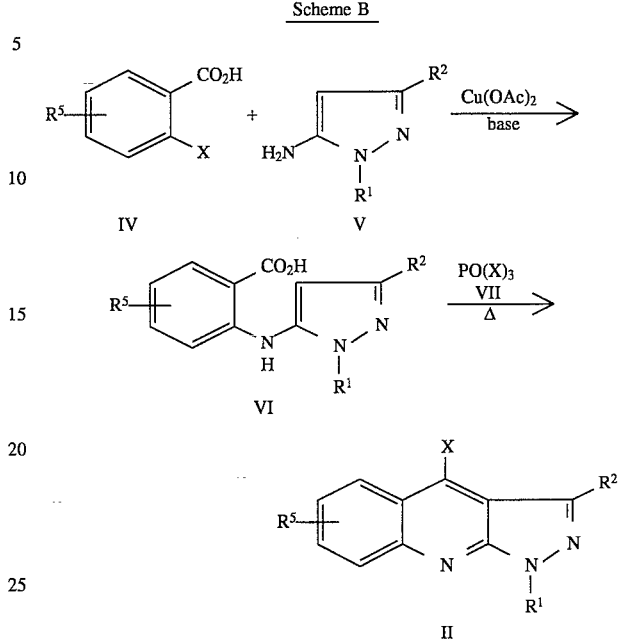

A suitably substituted benzoic acid derivative of the formula IV, wherein X is a halogen, preferably iodine, bromine or chlorine, in a suitable organic solvent, such as dimethylformamide, is treated with at least one mole of a suitable base, such as potassium carbonate, at least one mole of a suitably substituted pyrazole derivative of the formula V and a catalytic amount of Cu(OAc)$_2$, at a temperature in the range of about room temperature up to the boiling point of the solvent used, preferably at the boiling point of the solvent used, to afford the suitably substituted anthranilic acid derivatives of the formula VI. The suitably substituted anthranilic acid derivative of the formula VI can then be treated with an excess of a phosporous oxyhalide of the formula VII, wherein X is a halogen, preferably chlorine, at a temperature in the range of about room temperature up to the boiling point of the reaction mixture, preferably at a temperature in the range of about 90° C. up to the boiling point of the reaction mixture, to afford the compounds of the formula II.

The suitably substituted amines of the formula III, the suitably substituted benzoic acid derivatives of the formula IV and the suitably substituted pyrazole derivatives of the formula V are either commercially available, or they can be prepared by procedures known in the art, or by the procedures described hereinbelow in the examples.

The structures of the compounds of the invention were established by the mode of synthesis, and by one or more of elemental analysis, and infrared, nuclear magnetic resonance and mass spectroscopy. The course of the reactions and the identity and homogenity of the products were assessed by one or more of thin layer chromatography (TLC), high pressure liquid chromatography (HPLC), or gas-liquid chromatography (GLC).

The following examples will further illustrate the invention without, however, limiting it thereto. All melting points (m.p.) are given in degrees centigrade (°C.) and are uncorrected.

EXAMPLE 1

(a)

To a solution of 2-iodobenzoic acid (54 g, 0.218 mol) in DMF (570 ml) was added potassium carbonate (33.4 g, 0.242 mol), followed by 5-amino-1-ethylpyrazole (24.2 g, 0.218 mol) and finally Cu(OAc)$_2$.H$_2$O (0.9 g, 0.0045 mol). The reaction mixture was refluxed overnight, cooled and then poured into ice-water. Acetic acid and HCl were added until a pH of about 4 was obtained. A precipitate formed which was collected by filtration, washed with water and dried to afford 21.4 g of N-(1-ethylpyrazol-5-yl) anthranilic acid.

(b)

A mixture of N-(1-ethylpyrazol-5-yl)anthranilic acid (21.4 g, 0.0925 mol) and phosphorous oxychloride (312.8 g, 2.04 mol) was refluxed for 3 hours and then was stirred at room temperature overnight. The POCl$_3$ was removed by distillation, and the residue was poured into ice-water. The solution was neutralized with 35% NaOH and extracted with CH$_2$Cl$_2$ (4×). The organic layer was separated, washed with water, then brine and then was dried over MgSO$_4$. The solvent was concentrated in vacuo and the residue was purified by column chromatography on silica gel eluting with CH$_2$Cl$_2$ to afford 17.5 g (81.7%) of 4-chloro-1-ethyl-1H-pyrazolo[ 3,4-b]quinoline. Alternatively, the reaction was run as described above and then was worked up by neutralization with concentrated NH$_4$OH to a pH of 8 and then the product, which crystallized directly from the solution, was collected by filtration.

(c)

To a mixture of 4-chloro-1-ethyl-1H-pyrazolo[3,4-b] quinoline (10 g, 0.043 mol) and DMSO (75 ml) was added cyclohexanemethylamine (10.75 g, 0.095 mol). The reaction mixture was refluxed for about four hours, then was allowed to stand for about 2 days. About 40–50 ml of the DMSO was removed in vacuo and the residue was pured into ice-water. A precipitate formed which was collected by filtration, washed with water and dried. The solid precipitate was dissolved in CH$_2$Cl$_2$, washed with water, then brine and was then dried over MgSO$_4$. The solvent was filtered and concentrated in vacuo and the residue was purified by column chromatography on silica gel eluting with ethyl acetate/ cyclohexane (3/7) followed by recrystallization from hexane to afford 12 g (90.2%) of 1-ethyl-N-(cyclohexylmethyl)-1H-pyrazolo[ 3,4-b]quinolin-4-amine, as light yellow crystals, m.p. 161°–163° C.

(d)

1-ethyl-N-(cyclohexylmethyl)-1H-pyrazolo[3,4-b]quinolin-4-amine was dissolved in warm methanol and treated with CH$_3$SO$_3$H. A solid formed which was collected by filtration and recrystallized from isopropanol/ether to afford 1-ethyl-N-(cyclohexylmethyl)-1H-pyrazolo[ 3,4-b]quinolin-4-amine.CH$_3$SO$_3$H, m.p. 215–°217° C.

EXAMPLE 2

(a)

A mixture of 2-iodobenzoic acid (14.88 g, 0.06 mol), 1-ethyl- 3-methyl-5-aminopyrazole (7.5 g, 0.06 mol), DMF (50 ml), Cu(OAc)$_2$.H$_2$O (0.5 g) and potassium carbonate (8.3 g, 0.06 mol) was refluxed for 20 hours. The reaction mixture was cooled to room temperature, poured into ice-water and neutralized with acetic acid. A solid formed which was collected by filtration, washed with water and dried to give 7.1 g (98%) of N- (1-ethyl-3-methylpyrazol- 5-yl) anthranilic acid.

(b)

A mixture of N-(1-ethyl-3-methylpyrazol-5-yl) anthranilic acid (7.0 g), 28.57 mmol) and POCl$_3$ (210 ml) was refluxed for 24 hours. The reaction mixture was cooled to room temperature, poured into ice-water and neutralized with concentrated NH$_4$OH to a pH of 8.0. The product which slowly crystallized from the solution was collected by filtration, washed with water and dried to afford 6.7 g (95%) of 4-chloro-1-ethyl-3-methyl-1H-pyrazolo[3,4-b]quinoline.

(c)

A mixture of 4-chloro-1-ethyl-3-methyl-1H-pyrazolo[3, 4-b]quinoline (1.0 g, 0.0043 mmol), cyclohexanemethylamine (1.2 ml, 0.009 mol) and DMSO (3 ml) was heated at 80° C. overnight. The reaction mixture was pured into water (100 ml)/NH$_4$OH (0.5 ml) and was extracted with CH$_2$Cl$_2$. The solvent was evaporated to about 20 ml and then the mixture was purified by chromatography on silica gel, followed by high pressure liquid chromatography eluting with 20% EtOAc/hexane to 50% EtOAc/hexane to afford the product as the free base. The free base was dissolved in CH$_2$Cl$_2$ (20 ml) and treated with ethereal HCl and the solution was evaporated. The residue was crystallized from ethyl acetate/ether/ethanol to afford 1-ethyl-3-methyl-N-(cyclohexylmethyl)-1H-pyrazolo[3,4-b]quinolin- 4-amine hydrochloride, m.p. 215°–217° C.

EXAMPLE 3

A mixture of 4-chloro-1-ethyl-1H-pyrazolo[3,4-b]quinoline (3.0 g), trans-4-(aminomethyl)cyclohexane carboxylic acid (4.11 g) and DMSO (9 ml) was heated at 110°–120° C. overnight and then at reflux for 8 hours. The reaction mixture was cooled, partitioned between CH$_2$Cl$_2$ (100 ml)/ ethanol (20 ml)/water (100 ml) and then the layers were separated. The organic layer was washed with water, dried over MgSO$_4$, filtered and evaporated. The residue was passed through a silica gel column, and the filtrate was concentrated to afford an oil which was crystallized from hexane. The solid product was dissolved in methanol and treated with methanesulfonic acid and then the methanol was removed. The residue was crystallized from 2-propanol and the product was collected by filtration, washed with ether and dried to afford 0.6 g of 1-ethyl-N-[(4-methoxycarbonyl cyclohexyl)methyl]-1H-pyrazolo[ 3,4-b]quinolin-4-amine CH$_3$SO$_3$H, m.p. 232°–233° C.

EXAMPLE 4

Aminomethylcyclopropane hydrochloride (2.14 g, 0.02 mol) was treated with KOH/water/ether and then the ether layer was separated and the ether was distilled off to afford aminomethyl cyclopropane as the free base which was then treated with 4-chloro- 1-ethyl-1H-pyrazolo[3,4-b]quinoline (1.0 g, 0.0043 mol) and DMSO (3 ml). The mixture was stirred at 110° C. for about 4 days, cooled and partitioned between CH$_2$Cl$_2$ and water. The CH$_2$Cl$_2$ layer was concentrated and then the residue was purified by column chromatography on silica gel. The solid product was dissolved in methanol, treated with methanesulfonic acid and the methanol was removed. The residue was crystallized from 2-propanol and then recrystallized from 2-propanol to afford 1.0 g of 1-ethyl-N-(cyclopropylmethyl)- 1H-pyrazolo[3,4-b]quinolin-4-amine, m.p. 228°–230° C.

EXAMPLE 5

A mixture of 4-chloro-1-ethyl-1H-pyrazolo[3,4-b]quinoline (3 g), DMSO (9 ml) and trans-4-(aminomethyl)cyclohexane carboxylic acid (4.1 g) was heated at 180° C. overnight. The reaction mixture was then partitioned between $CH_2Cl_2$ and water, the layers were separated and the aqueous layer was extracted with $CH_2Cl_2$. The organic layers were combined, washed with water, dried over $Na_2SO_4$, and evaporated. The residue was purified by column chromatography on silca gel to afford an oil which was crystallized from ether/hexane and then recrystallized from ether/hexane to afford 1-ethyl-N-[[4-(methylthiomethoxycarbonyl) cyclohexyl]methyl]-1H-pyrazolo[3,4-b]quinolin-4-amine, m.p. 135°–136° C.

EXAMPLE 6

(a)

A mixture of 4-chloro-1-ethyl-1H-pyrazolo[3,4-b]quinoline (7 g, 0.03 mol), DMSO (20 ml) and trans-4-(aminomethyl) cyclohexane carboxylic acid was heated at 170°–180° C. for about 2 days. The reaction mixture was cooled, poured into 2N HCl (200 ml) and then was stirred for ½ hour and then allowed to stand for 2–3 hours. The solution was then poured into water, basified with NaOH and extracted with $CH_2Cl_2$ (2×50 ml). The aqueous layer was then brought to a pH of 5 and the water was decanted. The residual black gum which remained was dissolved in ethanol and cooled in an ice-bath. A solid formed which was collected by filtration and suspended in hot ethanol. The product was collected by filtration and dried to afford 1-ethyl-N-[(4-carboxycyclohexane)methyl]-1H-pyrazolo[ 3,4-b]quinolin-4-amine.

(b)

A mixture of 1-ethyl-N-[(4-carboxycyclohexyl)methyl]-1H-pyrazolo[ 3,4-b]quinolin-4-amine (5.0 g), THF (100 ml) and lithium aluminum hydride (3.0 g) was refluxed overnight. Additional lithium aluminum hydride (1.0 g) was added and the mixture was heated at reflux for another hour. The reaction mixture was cooled, water (4 ml), then 10% NaOH (4 ml) and finally water (12 ml) were added and the mixture was heated to reflux and then filtered. The collected solids were heated at reflux in THF for 10 minutes, then filtered again. The filtrates were combined, dried over $MgSO_4$ and then evaporated. The residue was purified by column chromatography on silica gel eluting with ethyl acetate and then was crystallized from hexanes/ethyl acetate. The product was dissolved in methanol, treated with methanesulfonic acid and then the methanol was evaporated. The residue was crystallized from 2-propanol and then recrystallized from 2-propanol to afford 1-ethyl-N-[( 4-hydroxy methylcyclohexyl)methyl]-1H-pyrazolo[3,4-b]quinolin-4-amine.$CH_3SO_3H$, as a white solid, m.p. 188°–190° C.

EXAMPLE 7

(a)

To m-anisic acid in acetic acid (1 L) was added dropwise bromine (85 ml), followed by water (1 L). The reaction mixture was heated to reflux, cooled in an ice-bath and then the product was collected by filtration, washed with cold water and dried to afford 2-bromo-5-methoxybenzoic acid, m.p. 154°–156° C.

(b)

A mixture of 2-bromo-5-methoxybenzoic acid (39.3 g, 0.17 mol), DMF (150 ml), 5-amino-1-ethylpyrazole (18.5 g, 0.17 mol), potassium carbonate (23.5 g, 0.17 mol) and $Cu(OAc)_2$ (0.6 g) was refluxed for about 2 days. The reaction mixture was cooled, poured into water and acidified to a pH of 5. A precipitate formed which was collected by filtration, washed with water and dried to afford 44.37 g (62%) of N-(1-ethylpyrazol-5-yl)-5-methoxyanthranilic acid.

(c)

A mixture of N-(1-ethylpyrazol-5-yl)-5-methoxyanthranilic acid (27.5 g, 0.105 mol) and $POCl_3$ (60 ml) was refluxed overnight. The reaction mixture was poured into ice-water, basified with $NH_4OH$ and the solid which formed was collected by filtration to afford 20 g of 4-chloro-1-ethyl-6-methoxy-1H-pyrazolo[3,4-b]quinoline.

(d)

A mixture of 4-chloro-1-ethyl-6-methoxy-1H-pyrazolo[3,4-b]quinoline (7.83 g, 0.03 mol), cyclohexanemethylamine (7.8 ml, 0.06 mol) and DMSO was heated at 110° C. overnight. The reaction mixture was cooled, poured into water and the solid which crystallized was collected by filtration and dried to afford 6.6 g (66%) of the product as the free base. The free base (0.8 g) was converted into the methanesulfonic acid salt which was recrystallized from 2-propanol to afford 800 mg of 1-ethyl-6-methoxy-N-(cyclohexylmethyl)- 1H-pyrazolo[3,4-b]quinolin-4-amine, m.p. 235°–237° C. Alternatively, the product can be isolated by pouring the reaction mixture into water, basifying with $NH_4OH$ to a pH of about 8, extracting with $CH_2Cl_2$, drying the $CH_2Cl_2$ layer over $MgSO_4$ and evaporating the $CH_2Cl_2$; followed by purification of the residue by column chromatography on silica gel eluting with ethyl acetate.

EXAMPLE 8

A mixture of 1-ethyl-6-methoxy-N-(cyclohexylmethyl)-1H-pyrazolo[ 3,4-b]quinolin-4-amine (5.4 g, 0.016 mol), boron tribromide (48 ml, 0.048 mol) and 1,2-dichloroethane (250 ml) was stirred at room temperature overnight. The reaction mixture was stirred with 1 volume of water, made basic with NaOH and the layers were separated. The basic layer was acidified with acetic acid and the yellow precipitate which formed was collected by filtration, washed with water and dried. The product was recrystallized from hot acetonitrile/methanol to afford 1-ethyl-6-hydroxy-N-(cyclohexylmethyl)- 1H-pyrazolo[3,4-b]quinolin-4-amine, as a yellow powder, m.p. 223°–224° C.

EXAMPLE 9

(a)

To a solution of acrylonitrile (122 ml, 2 mol) in ethanol (500 ml) in an ice-bath was added dropwise hydrazine hydrate (100 ml). The reaction mixture was stirred for 2 hours, then acetaldehyde (111.7 ml, 2.0 mol) was added and the mixture was stirred overnight. The ethanol was evaporated to afford $NCCH_2CH_2NH—N=CH(CH_3)$, which was used directly in the next step.

(b)

Sodium metal (50.6 g, 2.2 mol) was added to 1-butanol (2 L) and once all of the sodium metal dissolved the product of example 9 (a) [NCCH$_2$CH$_2$NH—N=CH(CH$_3$)] was added and the reaction mixture was refluxed overnight. The excess butanol was evaporated, 1 volume of water was added and the layers were separated. The aqueous layer was washed with ether and the organic layers were combined, washed with brine and evaporated. The residue was vacuum distilled to afford 42 g of 5-amino-1-ethylpyrazole.

(c)

A mixture of 3-methoxyanthranilic acid (16 g) and 10% sulfuric acid (250 ml) was warmed on a stream bath to effect a partial solution and then was rapidly cooled to 0°–3° C. and NaNO$_2$ (7 g) in water (20 ml) was added dropwise. The reaction mixture was stirred for 30 minutes then potassium iodide (24 g) in water (40 ml) was added and the mixture was allowed to warm 40°–50° C. over 3–4 hours and then was heated briefly at 60° C. The reaction mixture was extracted with ether, and the ether layer was washed with 5% NaOH. The aqueous layer was acidified with 2N HCl and extracted with ether. The ether was evaporated to afford 4 g of a mixture of 2-iodo-3-methoxybenzoic acid and 3-methoxybenzoic acid.

(d)

A mixture of 5-amino-1-ethylpyrazole (1.6 g, 0.0144 mol), DMF (40 ml), potassium carbonate (2 g), Cu(OAc)$_2$ (0.05 g), and 2-iodo- 3-methoxybenzoic acid/3-methoxybenzoic acid (4 g) of example 9 (c) was refluxed overnight. The reaction mixture was poured into water (200 ml) and acidified to pH 5 with acetic acid. The aqueous solution was extracted with ether (100–150 ml×5) and the aqueous layers were evaporated in vacuo. The residue from the aqueous layer was taken up in CH$_2$Cl$_2$, filtered and the organic filtrate was combined with the ether layer above and the mixture was evaporated in vacuo to afford 3-4 g of crude N-(1-ethylpyrazol-5-yl)- 3-methoxy anthranilic acid, which was used directly in the next step.

(e)

A mixture of N-(1-ethylpyrazol-5-yl)-3-methoxyanthranilic acid of example 9(d) and POCl$_3$ (50 ml) was refluxed overnight. The reaction mixture was poured into ice-water, neutralized with NH$_4$OH and the mixture was extracted with CH$_2$Cl$_2$ (3×150 ml). The CH$_2$Cl$_2$ extracts were combined, dried over MgSO$_4$, filtered and evaporated. The residue was purified by column chromatography on silica gel eluting with 35% EtOAc/hexane to afford 0.4 g of 4-chloro-1-ethyl-8-methoxy-1H-pyrazolo[3,4-b]quinoline, m.p. 168°–170° C.

(f)

A mixture of 4-chloro-1-ethyl-8-methoxy-1H-pyrazolo[3,4-b]quinoline (0.4 g, 1.53 mmol), DMSO (1 ml) and cyclohexanemethylamine (0.4 ml, 3.06 mmol) was heated at 150° C for 4 hours and then was stirred overnight at room temperature. The reaction mixture was partitioned between CH$_2$Cl$_2$ water, a few drops of NH$_4$OH were added, and then the CH$_2$Cl$_2$ layer was evaporated to afford a residue which crystallized from CH$_2$Cl$_2$ hexane. The solid product was treated with methanesulfonic acid and methanol, the methanol was evaporated and the residue was crystallized from 2propanol/ether and then recrystallized from 2-propanol/ether to afford 0.18 g of 1-ethyl-8-methoxy-N-(cyclohexylmethyl)-1H-pyrazolo[ 3,4-b]quinolin-4-amine CH$_3$SO$_3$H, m.p. 222°–225° C.

EXAMPLE 10

(a)

A mixture of acrylonitrile (15.3 g, 0.289 mol) and ethanol (75 ml) was stirred in an ice-bath and then hydrazine hydrate (15 ml, 0.3 mol) was added dropwise and the mixture was warmed to room temperature and stirred for 2 hours. Benzaldehyde (30.6 ml, 0.3 mol) was then added and the reaction mixture was stirred at room temperature for about 2 days. The react ion mixture was concentrated in vacuo and the residue was added to a solution of sodium butoxide in butanol [prepared from sodium metal (6.9 g) and butanol (300 ml)]. The reaction mixture was refluxed overnight and then the solvent was concentrated in vacuo to afford 19.4 g of crude 5-amino-1-phenyl methylpyrazole.

(b)

A mixture of 2-iodobenzoic acid (14 g, 0.057 mol), 5-amino- 1-phenylmethylpyrazole (9.8 g, 0.057 mol), DMF (140 ml), potassium carbonate (8.3 g) and Cu(OAc)2 (0.1 g) was refluxed for about 2 days. The reaction mixture was poured into water, acidified with acetic acid to a pH of 5 and then the solid which formed was collected by filtration, washed with water, then ether and then was dried to afford N-(1-phenylmethylpyrazol-5-yl) anthranilic acid, m.p. 190° C.

(c)

A mixture of N-(1-phenylmethylpyrazol-5-yl) anthranilic acid (6 g) and POCl$_3$ (60 ml) was heated on a steam bath overnight. The reaction mixture was poured into ice-water, neutralized with NH$_4$OH and the precipitate which formed was collected by filtration, washed with water and dried to afford 5 g of 1-phenylmethyl- 4-chloro-1H-pyrazolo[3,4-b]quinoline, as a light brown powder.

(d)

A mixture of 1-phenylmethyl-4-chloro-1H-pyrazolo[3,4-b]quinoline ( 3.0 g, 10.2 mmol), DMSO (10 ml) and cyclohexanemethylamine (2.63 ml, 20.5 mmol) was heated at 110° C. for 4 hours and then was allowed to sit at room temperature overnight. The reaction mixture was partitioned between CH$_2$Cl$_2$/water and the organic layer was separated and evaporated. The residue was purified by column chromatography on silica gel eluting with 25% ethyl acetate/hexane to afford 2.5 g of the product as the free base. The free base (0.6 g) was treated with methanesulfonic acid/methanol to afford the CH$_3$SO$_3$H salt which was recrystallized from 2-propanol/ether to afford 1.22 g of 1-phenylmethyl-N-(cyclohexylmethyl)- 1H-pyrazolo[3,4-b]quinolin-4-amine.CH$_3$SO$_3$H, as a beige solid, m.p. 254°–256° C.

Example 11

(a)

A mixture of acrylonitrile (17.4 ml, 0.264 mol), ethanol (160 ml) and hydrazine hydrate (13.2 ml, 0.264 mol) were stirred for 2 hours and then cyclopentanone (24.8 ml, 0.28 mol) was added and the mixture was stirred overnight. The ethanol was evaporated to afford crude NCCH$_2$CH$_2$NH—N=cyclopentyl, which was used directly in the next step.

(b)

A mixture of 1-butanol (400 ml) and sodium metal (6.5 g, 0.28 mol) was stirred until all of the sodium metal had dissolved and then the product of example 11 (a) [NCCH$_2$CH$_2$NH—N=cyclopentyl] was added. The reaction mixture was refluxed overnight, the excess 1-butanol was evaporated and water was added. The water layer was separated and the residue was again treated with water. The water layers were combined and extracted with ether. The ether layer was washed with brine and then evaporated. The residue was purified by Kuglerohr distillation (2×) at 80°–120° C. and 1 mm Hg to afford 22.3 g of 5-amino-1-cyclopentylpyrazole, as a clear oil.

(c)

A mixture of 2-iodobenzoic acid (28 g, 0.113 mol), 5-amino- 1-cyclopentylpyrazole (17 g, 0.113 mol), DMF (100 ml), potassium carbonate (16 g, 0.113 mol) and Cu(OAc) 2 (0.5 g) was refluxed overnight. The reaction mixture was poured into ice-water, and acidified with acetic acid to a pH of 5. The gum which formed was extracted with CH$_2$Cl$_2$ and the CH$_2$Cl$_2$ layer was washed with water, dried over MgSO$_4$, and evaporated to afford 21 g of N-(1-cyclopentyl pyrazol-5-yl) anthranilic acid.

(d)

A mixture of N-(1-cyclopentylpyrazol-5-yl) anthranilic acid (21 g, 0.0775 mol) and POCl$_3$ (100 ml) was refluxed for 8 hours. The reaction mixture was poured into ice-water and neutralized with NH$_4$OH. A gum formed which was extracted with CH$_2$Cl$_2$. The CH$_2$Cl$_2$ layer was then washed with water, dried over MgSO$_4$, filtered and concentrated. The residue was purified by column chromatography on silica gel eluting with 40% to 70% CH$_2$Cl$_2$/hexane to afford 7.5 g of 4-chloro-1-cyclopentyl-1H-pyrazolo[ 3,4-b]quinoline, m.p. 97°–98 ° C.

(e)

A mixture of 4-chloro-1-cyclopentyl-1H-pyrazolo[3,4-b]quinoline (1 g, 0.0037 mol), DMSO (2 ml) and cyclohexanemethylamine (0.96 ml, 0.0075 mol) was heated at 110° C. for 4 hours and then was allowed to stand overnight. The reaction mixture was partitioned between water/CH$_2$Cl$_2$, and the CH$_2$Cl$_2$ layer was separated and evaporated. The residue was purified by column chromatography on silca gel eluting with 25% ethyl acetate/hexane to afford 1.2 g of the product as the free base. The free base was treated with methanesulfonic acid/methanol and the methanesulfonic acid salt was crystallized from 2-propanol/ether to afford 722 mg of 1-cyclopentyl-N-(cyclohexylmethyl)-1H-pyrazolo[3,4-b]quinolin-4-amine, m.p. 290°–292° C.

EXAMPLE 12

A mixture of 1-ethyl-6-hydroxy-N-(cyclohexylmethyl)-1H-pyrazolo[ 3,4-b]quinolin-4-amine (2 g, 0.0062 mol), KOH (2 g), DMSO (35 ml) and dimethylaminoethyl chloride (0.7 g, 0.0065 mol) was stirred at room temperature for 4 hours and then was allowed to stand overnight. The reaction mixture was partitioned between CH$_2$Cl$_2$ (75 ml) and water (75 ml), the layers were separated and the aqueous layer was extracted with CH$_2$Cl$_2$ (2×). The CH$_2$Cl$_2$ layers were combined, dried over K$_2$CO$_3$ and evaporated. The residue was purified by column chromatography on silica gel eluting with 50% ether/methanol, followed by a second column chromatography eluting with 25% methanol/ether to afford the product as the free base. The free base was taken up in methanol, treated with methanesulfonic acid and the methanol was evaporated. The residue was crystallized from hot 2-propanol/ether and then was recrystallized from hot 2-propanol/ether to afford 696 mg of 1-ethyl- 6-[2-(dimethylamino)ethoxy]-N-(cyclohexymethyl)-1H-pyrazolo[ 3,4-b]quinolin-4-amine.2-CH$_3$SO$_3$H, m.p. 186°–188° C.

EXAMPLE 13

A mixture of 1-ethyl-6-hydroxy-N-(cyclohexymethyl)-1H-pyrazolo[ 3,4-b]quinolin-4-amine (2.0 g, 6.2 mmol), DMSO (30 ml), ethylbromoacetate (0.67 ml, 6 mmol) and KOH (2 g) was stirred at room temperature overnight. The reaction mixture was poured into water and acidified with acetic acid to a pH of about 5. A solid formed which was collected by filtration, washed with water and then stirred with hot ethyl acetate/CH$_2$Cl$_2$. The mixture was filtered and washed with ether to afford 1.5 g of 1-ethyl-6-(carboxymethoxy)-N-(cyclohexymethyl)- 1H-pyrazolo[3,4-b]quinolin-4-amine. ¾ hydrate, m.p. 280° C. (dec.).

EXAMPLE 14

A mixture of 4-chloro-1-ethyl-1H-pyrazolo[3,4-b]quinoline (1 g), DMSO (3 ml) and adamantylmethylamine (1 g) was heated at 110° C. overnight. The reaction mixture was poured into water, and a precipitate formed which was collected by filtration and dried to afford the product as a free base. The free base was treated with methanesulfonic acid/methanol, the methanol was evaporated and the salt was recrystallized from 2-propanol to afford 290 mg of 1-ethyl-N-(adamantylmethyl)-1H-pyrazolo[3,4-b]quinolin-4-amine.CH$_3$SO$_3$H, m.p. 310° C.

EXAMPLE 15

(a)

A mixture of 2-chloro-5-nitrobenzoic acid (4.03 g, 0.02 mol), 5-amino-1-ethylpyrazole (2.22 g, 0.02 mol), DMF (25 ml), K$_2$CO$_3$ (2.76 g, 0.02 mol) and Cu(OAc)$_2$.H$_2$O (0.5 g) was refluxed for 24 hours. The reaction mixture was cooled to room temperature, poured into ice-water and acidified with acetic acid to a pH of 5. A solid formed which was collected by filtration and dried to afford 3.8 g (68%) of N-(1-ethylpyrazol-5-yl)-5-nitroanthranilic acid.

(b)

A mixture of N-(1-ethylpyrazol-5-yl)-5-nitroanthranilic acid (3.8 g, 13.77 mmol) and POCl$_3$ (20 ml) was refluxed for 8 hours. The reaction mixture was poured into ice-water, neutralized with concentrated NH$_4$OH and the resulting solid was collected by filtration, washed with water and dried to afford 2.5 g (65%) of 1-ethyl-4-chloro-6-nitro-1H-pyrazolo[3,4-b]quinoline.

(c)

A mixture of 1-ethyl-4-chloro-6-nitro-1H-pyrazolo[3,4-b]quinoline ( 2.2 g, 7.95 mmol), DMSO (10 ml) and cyclohexanemethylamine (1.8 g, 16 mmol) was heated at 120°–130° C. for 18 hours. The reaction mixture was cooled to room temperature, and poured into ice-water. A solid formed which was collected by filtration and dried to afford 2.9 g of the product as the free base. The free base (0.6 g) was dissolved in hot methanol, cooled to room temperature and then treated with one equivalent of methanesulfonic acid. Ether was added to the mixture and the solid which formed was collected by filtration and recrystallized from methanol/ether to afford 0.5 g of 1-ethyl-6-nitro-N-(cyclohexylmethyl) - 1H-pyrazolo[3,4-b]quinolin-4-amine.CH₃SO₃H, m.p. 261°–263° (dec.).

EXAMPLE 16

(a)

A mixture of 2-chloro-4-nitrobenzoic acid (4.03 g, 0.02 mol), 5-amino-1-ethylpyrazole (2.22 g, 0.02 mol), DMF (25 ml), K₂CO₃ (2.76 g, 0.02 mol) and Cu(OAc)₂.H₂O (0.5 g) was refluxed for 24 hours. The reaction mixture was cooled to room temperature, poured into ice-water and then acidified with acetic acid to a pH of 5. A solid formed which was collected by filtration and dried to afford 3.5 g (63%) of N-(1-ethylpyrazol-5-yl)-4-nitroanthranilic acid.

(b)

A mixture of N-(1-ethylpyrazol-5-yl) -4-nitroanthranilic acid (3.4 g, 12.32 mmol) and POCl₃ (20 ml) was refluxed for 8 hours. The reaction mixture was poured into ice-water, neutralized with concentrated NH₄OH and the resulting solid was collected by filtration, washed with water and dried to afford 2.8 g (82%) of 1-ethyl-4-chloro-7-nitro-1H-pyrazolo[3,4-b]quinoline.

(c)

A mixture of 1-ethyl-4-chloro-7-nitro-1H-pyrazolo[3,4b] quinoline ( 2.5 g, 9.04 mmol), DMSO (10 ml) and cyclohexanemethylamine (2.05 g, 18.1 mmol) was heated at 120°–130° C. for 18 hours. The reaction mixture was cooled to room temperature, poured into ice-water and the resulting solid was collected by filtration and dried to afford 3.0 g of crude product. The product was purified by column chromatography on silica gel eluting with CH₂Cl₂ ether (4/1) to afford 2.2 g (69%) of 1-ethyl-7-nitro-N-(cyclohexylmethyl)-1H-pyrazolo[3,4-b]quinolin-4-amine, m.p. 205°–207° C.

EXAMPLE 17

(a)

A mixture of 1-ethyl-6-hydroxy-N-(cyclohexylmethyl)-1H-pyrazolo[ 3,4-b]quinolin-4-amine (6 g), KOH (5 g), and DMSO (70 ml) was stirred for 30 minutes and then epichlorohydrin (1.5 ml) was added. The reaction mixture was stirred overnight and then was partitioned between CH₂Cl₂ and water. The organic layer was then separated, dried and evaporated to dryness. The residue was purified by column chromatography on silica gel eluting with ethyl acetate, followed by crystallization from hexane/ether to afford 1.0 g of 1-ethyl-6-(2,3-epoxypropoxy)-N-(cyclohexylmethyl)-1H-pyrazolo[ 3,4-b]quinolin-4-amine, m.p. 160°–163° C.

(b)

A mixture of 1-ethyl-6-(2,3-epoxypropoxy)-N-(cyclohexylmethyl)- 1H-pyrazolo[3,4-b]quinolin-4-amine (0.53 g) and formic acid (10 ml) were stirred at room temperature overnight. The excess formic acid was removed in vacuo and then methanol (75 ml) and triethylamine (10 ml) were added and the mixture was stirred for four hours. The reaction mixture was evaporated, ether was added and the product which crystallized was recrystallized from CH₂Cl₂/Et₂O and then purified by column chromatography on silca eluting with CH₂Cl₂/THF (1/1) to afford 1-ethyl-6-(2,3-dihydroxypropoxy)-N-(cyclohexylmethyl)- 1H-pyrazolo[3,4-b]quinolin-4-amine, m.p. 197°–199° C.

EXAMPLE 18

(a)

A mixture of 2-nitro-4-methoxybenzoic acid (21.9 g, 0.111 mol), 2N ammonium hydroxide (250 ml) and 5% palladium on strontium carbonate (2.5 g) was shaken under 45 psi of hydrogen pressure for 3–4 hours. The reaction mixture was filtered, and the filtrate was acidified with acetic acid. A solid formed which was collected by filtration, washed with water and dried to afford 16 g of 4-methoxyanthranilic acid, m.p. 194°–195° C.

(b)

To a mixture of 50% sulfuric acid (150 ml) and 4-methoxyanthranilic acid (12 g) at 5°–10° C. was added sodium nitrite (5.5 g) in water, followed 10 minutes later by NaI (16.5 g) in water (30–50 ml). The reaction mixture was warmed to room temperature and stirred for 2 hours, then was heated at 60°–70° C. for 10 minutes, followed by stirring at room temperature for 1 hour. The reaction mixture was extracted with ether (4×125 ml) and the combined ether extracts were washed with water (50 ml×2), dried over MgSO₄, filtered and evaporated. The residue was purified by column chromatography on silica gel eluting with ether to afford 12 g of 2-iodo-4-methoxybenzoic acid.

(c)

A mixture of 2-iodo-4-methoxybenzoic acid (13.6 g, 48.9 mmol), 5-amino-1-ethylpyrazole (5.5 g, 49 mmol), DMF (100 ml), K₂CO₃ (6.9 g, 0.05 mol) and Cu(OAc)₂ (0.5 g) was refluxed overnight. The reaction mixture was poured into water (500 ml) and acidified with acetic acid to a pH of 5–6. The product slowly crystallized from the solution and was collected by filtration and washed with water. The solid was taken up in CH₂Cl₂/methanol, dried, filtered and evaporated. The residue was combined with POCl₃ (60 ml) and refluxed overnight. The reaction mixture was cooled, poured into water and neutralized with concentrated NH₄OH. The mixture was extracted with CH₂Cl₂, and the CH₂Cl₂ extracts were evaporated and the residue was purified by column chromatography on silica gel eluting with ethyl acetate to afford 5 g of 1-ethyl-4-chloro-7-methoxy-1H-pyrazolo[3,4-b]quinoline, m.p. 114°–115° C.

(d)

A mixture of 1-ethyl-4-chloro-7-methoxy-1H-pyrazolo[3,4-b]quinoline (4.0 g, 15.3 mmol), cyclohexanemethylamine (3.74 g, 33 mmol) and DMSO (12 ml) was heated at 110° C. overnight. The reaction mixture was poured into water (200 ml) and the solid which formed was collected by filtration. The filtrate was extracted with CH₂Cl₂ (40 ml) and the solid was added to the CH₂Cl₂ and the solution was dried over MgSO₄. The CH₂Cl₂ was evaporated to 20–30 ml and then was passed through a silica gel column eluting with ethyl acetate to afford 4 g of the product as the free base. The free base was treated with methanesulfonic acid/methanol to afford 1-ethyl-7-methoxy-N-(cyclohexylmethyl)-1H-pyrazolo[3,4-b]quinolin-4-amine.CH$_3$SO$_3$H.

EXAMPLE 19

(a)

To a solution of benzylamine (12.8 g, 0.12 mol) in toluene (120 ml) at 0° C. was added trimethyl aluminum (60 ml, 0.12 mol, 2M in toluene). The reaction mixture was stirred at room temperature for 1 hour, then was cooled to 0° C. and then ethyl 4-hydroxycylcohexylcarboxylate (10.32 g, 0.06 mol) in toluene (250 ml) was added and the reaction mixture was stirred for about 2 days. The reaction mixture was poured into ice-water containing 2N HCl (300 ml) and was stirred for 30 minutes. The organic layer was separated, the aqueous layer was extracted with ethyl acetate (2×150 ml) and the combined organic layers were washed with brine and dried over MgSO$_4$. Removal of the solvent and tituration with hexane afforded 9.1g (64%) of N-benzyl-4-hydroxcyclohexylamide.

(b)

To a solution of N-benzyl-4-hydroxycyclohexylamide (9 g, 38.62 mmol) in THF (250 ml) was added lithium aluminum hydride (4.74 g, 125 mmol). The reaction mixture was stirred at room temperature for 30 minutes, then was relfuxed for 18 hours. The reaction mixture was cooled in an ice-bath, neutralized with saturated Na$_2$SO$_4$ and then filtered. The filtrate was evaporated to dryness to afford 8.5 g of N-benzyl-N-(4-hydroxycyclohexylmethyl) amine.

(c)

To a stirred solution of N-benzyl-N-(4-hydroxycyclohexyl methyl)amine (8.5 g, 0.039 mol) in methanol (300 ml) under N$_2$ was added ammonium formate (9.8 g, 0.0155 mol), followed by 10% palladium on carbon (1.0 g). The reaction mixture was refluxed for 3 hours, cooled to room temperature and filtered. The filtrate was evaporated to dryness and the residue was dissolved in CH$_2$Cl$_2$, filtered and the filtrate was evaporated to afford 1.3 g of 4-hydroxycyclohexylmethylamine.

(d)

A mixture of 4-hydroxycyclohexylmethylamine (2.2 g, 17.05 mmol), 1-ethyl-4-chloro-6-methoxy-1H-pyrazolo[3, 4-b]quinoline (2.0 g, 7.66 mmol) and DMSO was heated at 110°–120° C. under a nitrogen atmosphere for 16 hours. The reaction mixture was poured into ice-water and the mixture was extracted with CH$_2$Cl$_2$ (4×50 ml). The organic layers were combined, dried over MgSO$_4$ and evaporated to dryness. The residue was purified by column chromatography on silica gel eluting with CH$_2$Cl$_2$/methanol (9/1), followed by a second silica gel column eluting with ethyl acetate to afford 1.3 g of crude product. The crude product was dissolved in warm methanol, cooled to room temperature and treated with an equivalent amount of methanesuflonic acid. Ether was added to the mixture and the solid which formed was collected by filtration, washed with ether and recrystallized from isopropanol to afford 0.85 g of 1-ethyl-6-methoxy-N-(4-hydroxycyclohexylmethyl)-1H-pyrazolo[3,4-b]quinolin-4-amine.CH$_3$SO$_3$H, as yellow crystals, m.p. 256°–258° C. (dec.).

EXAMPLE 20

A mixture of 1-ethyl-6-nitro-N-(cyclohexylmethyl)-1H-pyrazolo[3,4-b]quinolin-4-amine (2.3 g, 6.51 mmol), methanol (20 ml), 10% palladium on carbon (0.3 g) and ammonium formate (1.9 g, 30 mmol) was stirred at room temperature under argon for 2 hours and then was heated on a steam bath for 3 hours. The reaction mixture was filtered, the filter cake was washed with methanol and the filtrate was evaporated to dryness. The residue was partitioned between CH$_2$Cl$_2$ and water, and the organic layer was separated, dried over MgSO$_4$ and evaporated to dryness. The residue was purified by column chromatography on silica gel eluting with CH$_2$Cl$_2$/MeOH (9/1) to afford 1.0 g (45%) of the product as the free base. The free base was dissolved in methanol and treated with one equivalent of methanesulfonic acid. Ether was added to the mixture and the resulting solid was collected by filtration and recrystallized from CH$_2$Cl$_2$/ether to afford 0.77 g of 1-ethyl- 6-amino-N-(cyclohexylmethyl)-1H-pyrazolo[3,4-b]quinolin-4-amine.CH$_3$SO$_3$H, m.p. 232°–234° C. (dec.).

EXAMPLE 21

A mixture of 1-ethyl-6-hydroxy-N-(cyclohexylmethyl)-1H-pyrazolo[ 3,4-b]quinolin-4-amine (2 g), DMSO (30 ml) and KOH (2 g) was stirred at room temperature for 0.5 hours, then epichlorohydrin (0.49 ml) was added and the mixture was stirred overnight. The reaction mixture was partitioned between CH$_2$Cl$_2$ and water, and then the CH$_2$Cl$_2$ layer was separated and evaporated. The residue was purified by column chromatography on silica gel eluting with ethyl acetate to afford the product which was combined with the product from a similar experimental. The combined material was purified further by column chromatography on silica gel eluting with 90% ether/t-butylmethylether, followed by crystallization from ether, to afford 1-ethyl-6-(2, 3-epoxypropoxy)-N-(cyclohexylmethyl)- 1H-pyrazolo[3,4-b]quinolin-4amine, m.p. 168°–170° C.

EXAMPLE 22

A mixture of 1-ethyl-6-hydroxy-N-(cyclohexylmethyl)-1H-pyrazolo[ 3,4-b]quinolin-4-amine (0.5 g, 1.5 mmol), DMSO (5 ml) and KOH (0.5 g) was stirred at room temperature for 20 minutes, then ethyl 2-bromopropionate (0.2 ml) was added and the mixture was stirred overnight. The reaction mixture was poured into 10 volumes of water, extracted with CH$_2$Cl$_2$ (2×10 ml) and the aqueous layer was acidified with acetic acid. A precipitate formed which was collected by filtration, dissolved in methanol and filtered. The filtrate was allowed to stand and the product which precipitated was collected by filtration and dried to afford 180 mg of 1-ethyl- 6-(1-carboxyethoxy)-N-(cyclohexylmethyl)-1H-pyrazolo[3,4-b]quinolin-4-amine.¼ hydrate, m.p. 280° C. (dec.).

EXAMPLE 23

(a)

A mixture of 2-bromoterephthalic acid (4.8 g, 0.02 mol), DMF (50 ml), Cu(OAc)$_2$ (0.2 g), 5-amino-1-ethylpyrazole (2.22 g, 0.02 mol) and K$_2$CO$_3$ (2.71 g, 0.02 mol) was heated at 135° C. overnight, then at reflux overnight. The reaction mixture was poured into water, acidified with acetic acid and the precipitate which formed was collected by filtration and dried to afford 2.5 g of N-(1-ethylpyrazol-5-yl)-4-carboxyanthranilic acid.

(b)

A mixture of N-(1-ethylpyrazol-5-yl)-4-carboxyanthranilic acid (2.5 g) and POCl₃ (20 ml) was refluxed overnight. The reaction mixture was poured into water, acidified with acetic acid and the solids which formed were collected by filtration. The solid was taken up in 10% NaOH, washed with ether and then the aqueous layer was acidified with concentrated HCl. The mixture was extracted with ether, the ether layer was dried over MgSO₄ filtered and evaporated to afford 1 g of 1-ethyl-4-chloro-7-carboxy- 1H-pyrazolo[3,4-b]quinoline, as a yellow powder.

(c)

A mixture of 1-ethyl-4-chloro-7-carboxy-1H-pyrazolo[3,4-b]quinoline (0.9 g, 3.3 mmol), DMSO (9 ml) and cyclohexanemethyl amine (0.86 ml, 6.6 mmol) was heated at 120°–130° C. for 6 hours. The reaction mixture was poured into water, acidified with acetic acid and the solid which formed was collected by filtration, dissolved in 5% NaOH and extracted with CH₂Cl₂ (2×50 ml). The aqueous layer was acidified with acetic acid and the solid which formed was collected by filtration and washed with water. The solid was purified by column chromatography on silica gel eluting with 30% methanol/10% acetic acid/60% CH₂Cl₂ to afford 1-ethyl-7-carboxy-N-(cyclohexylmethyl)- 1H-pyrazolo[3,4-b]quinolin-4-amine, as a yellow solid.

EXAMPLE 24

(a)

A mixture of 5-acetamido-2-bromobenzoic acid (7 g, 27 mmol), DMF (25 ml), Cu(OAc)₂ (0.2 g), 5-amino-1-ethylpyrazole (3 g, 27 mmol) and K₂CO₃ (3.7 g, 27 mmol) was refluxed for about 2 days. The reaction mixture was poured into water, acidified with acetic acid and cooled. A solid formed which was collected by filtration to afford 2 g of N-(1-ethylpyrazole-5-yl)-5-acetamidoanthranilic acid.

(b)

A mixture of N-(1-ethylpyrazole-5-yl)-5-acetamido anthranilic acid (2 g) and POCl₃ (20 ml) was refluxed overnight. The reaction mixture was poured into ice-water (400 ml), neutralized with NH₄OH and extracted with CH₂Cl₂ (3×100 ml). The CH₂Cl₂ layers were combined and concentrated in vacuo and the residue was purified by column chromatography on silica gel eluting with ethyl acetate to afford 0.2 g of 1-ethyl-4-chloro-6-acetamido-1H-pyrazolo[3,4-b]quinoline.

(c)

A mixture of 1-ethyl-4-chloro-6-acetamido-1H-pyrazolo [3,4-b]quinoline (0.2 g, 0.7 mmol), cyclohexanemethylamine (0.5 ml, 3.5 mmol) and DMSO (3 ml) was heated at 110° C. for 6 hours. The reaction mixture was poured into water (50 ml), extracted with CH₂Cl₂ (4×25 ml) and the organic layers were combined and evaporated. The residue was slurried in ether and a yellow solid was collected by filtration and recrystallized from ethanol/ethyl acetate to afford 200 mg of 1-ethyl-6-acetamido-N-(cyclohexylmethyl)- 1H-pyrazolo[3,4-b]quinolin-4-amine, m.p. 277°–278° C.

EXAMPLE 25

A mixture of 1-ethyl-7-nitro-N-(cyclohexylmethyl)-1H-pyrazolo[ 3,4-b]quinolin-4-amine (1.6 g, 4.53 mmol), methanol (150 ml), 10% palladium on carbon (100 mg) and CHCl₃ (1 ml) was hydrogenated on a Parr apparatus at 40 psi for 8 hours. The catalyst was removed by filtration and the filtrate was concentrated in vacuo. The residue was treated with concentrated NH₄OH and extracted with CH₂Cl₂ (2×50 ml). The CH₂Cl₂ layers were combined, dried over MgSO₄ and evaporated. The residue was dissolved in warm methanol and an equivalent amount of methanesulfonic acid was added. A solid formed which was collected by filtration and recrystallized from CH₂Cl₂/ether to afford 0.8 g of crude product. The crude product was dissolved in CH₂Cl₂, treated with NH₄OH and then the CH₂Cl₂ was evaporated to afford the product as the free base. The free base was purified by column chromatography on silica gel eluting with CH₂Cl₂/methanol (4/1) to afford 0.4 g of the purified free base, which was dissolved in methanol and treated with methanesulfonic acid to afford the methanesulfonic acid salt. The salt was recrystallized from isopropanol to afford 0.28 g of 1-ethyl-7-amino-N-(cyclohexylmethyl)- 1H-pyrazolo[3,4-b]quinolin-4-amine.CH₃SO₃H.¼ H₂O, m.p. 268°–270° C. (dec.).

EXAMPLE 26

A mixture of S (+)-1-cyclohexylethylamine (0.734 ml), 1-ethyl- 4-chloro-6-methoxy-1H-pyrazolo[3,4-b]quinoline (1.3 g, 5 mmol), DMSO (3 ml) and triethylamine (1.5 ml, 0.01 mol) was heated at 110° C. overnight. The reaction mixture was partitioned between CH₂Cl₂ and water and the CH₂Cl₂ layer was separated and evaporated to dryness. The residue was purified by column chromatography on silica gel eluting with 60% ethyl acetate/hexane to afford 0.4 g of the product as the free base. The free base was treated with ethanol/methanesulfonic acid to afford 0.251 g of 1-ethyl-6-methoxy-N-[S(+)- 1-(cyclohexyl)ethyl]-1H-pyrazolo[3,4-b]quinolin-4-amine.CH₃SO₃H. ½ H₂O, m.p. 159°–160° C., $[\alpha]^{25}D$= 71.6°. CHCl₃.

EXAMPLE 27

A mixture of R (−)-1-cyclohexylethylamine (0.734 ml). 1-ethyl- 4-chloro-6-methoxy-1H-pyrazolo[3,4-b]quinoline (1.3 g, 5 mmol), DMSO (3 ml) and triethylamine (1.5 ml, 0.01 mol) was heated at 110° C. overnight. The reaction mixture was partitioned between CH₂Cl₂ and water and the CH₂Cl₂ layer was separated and evaporated. The residue was purified by column chromatography on silica gel (2×) eluting with 60% ethyl acetate/hexane to afford the product as the free base. The free base was treated with methanol/methanesulfonic acid and the salt was crystallized from 2-propanol/ether to afford 0.4 g of 1-ethyl-6-methoxy-N-[R(−)-1-(cyclohexyl)ethyl]- 1H-pyrazolo[3,4-b]quinolin-4-amine.CH₃SO₃H.½ H₂O, m.p. 154°–160° C., $[\alpha]_{25}D$=−74.9°, CHCl₃.

EXAMPLE 28

(a)

A mixture of 1-ethyl-4-chloro-6-methoxy-1H-pyrazolo[3,4-b]quinoline (2.02 g, 15.5 mmol), DMSO (6 ml) and 4-hydroxy cyclohexylmethylamine (2 g, 15.5 mmol) was heated at 110° C. overnight. The reaction mixture was partitioned between CH₂Cl₂/water/NaHCO₃, and the CH₂Cl₂ layer was separated, dried over MgSO₄ and evaporated. The residue was purified by column chromatography on silica gel eluting with ethyl acetate to afford 1.8 g of 1-ethyl-6-methoxy-N-(4-hydroxycyclohexylmethyl) -1H-pyrazolo[ 3,4-b]quinolin-4-amine.

(b)

To a solution of $CH_2Cl_2$ (35 ml) and trifluoroacetic anhydride (3.6 ml, 0.0224 mol) at −78° C. was added $CH_2Cl_2$ (5 ml) and DMSO (3.22 ml, 0.0454 mol). The reaction mixture was stirred for 1 hour then a solution of 1-ethyl-6-methoxy-N-(4-hydroxycyclohexyl methyl)-1H-pyrazolo-[3,4-b]quinolin-4-amine (1.8 g, 0.0051 mol) in $CH_2Cl_2$ (30 ml) was added and the reaction mixture was slowly warmed to 0° C. with stirring overnight. The reaction mixture was cooled to −78° C. and triethylamine (11 ml, 0.075 mol) was added. The reaction mixture was warmed to room temperature, stirred for 5 hours and then poured into water. The mixture was extracted with $CH_2Cl_2$ and the $CH_2Cl_2$ extracts were combined, washed with water, dried over $MgSO_4$ and evaporated. The residue was purified by column chromatography on silica gel eluting with ethyl acetate to afford the product as the free base. The free base was dissolved in 2-propanol and methanesulfonic acid was added. The volume was reduced to about 5 ml, ether was added and the precipitated salt was collected by filtration and recrystallized from 2-propanol/ether to afford 1 g of 1-ethyl-6-methoxy-N-[ 4-oxocyclohexylmethyl]-1H-pyrazolo[3,4-b]quinolin-4-amine.$CH_3SO_3H.1/2 H_2O$.

EXAMPLE 29

(a)

A mixture of 2,5-dibromobenzoic acid (25 g, 0.09 mol), DMF (200 ml), 5-amino-1-ethylpyrazole (10 g, 0.09 mol), $Cu(OAc)_2$ (1 g) and $K_2CO_3$ (12.3 g, 0.09 mol) was heated at reflux for about 2 days. The reaction mixture was poured into water, acidified with acetic acid and the precipitate which formed was collected by filtration to afford 12.6 g of N-(1-ethylpyrazol-5-yl)-5-bromoanthranilic acid.

(b)

A mixture of N-(1-ethylpyrazol-5-yl)-5-bromoanthranilic acid (12.6 g) and $POCl_3$ (30 ml) was refluxed overnight. The reaction mixture was poured into ice-water (500 ml), stirred for 20 minutes, and then $NH_4OH$ was added until a pH of 8–10 was obtained. The mixture was stirred for 0.5 hours and then the solid which formed was collected by filtration. The solid was dissolved in $CH_2Cl_2$, dried over $MgSO_4$ and purified by column chromatography on silica gel eluting with 30% hexane/ethyl acetate to afford 6.5 g of 1-ethyl-4-chloro-6-bromo-1H-pyrazolo[3,4-b]quinoline, m.p. 117°–118° C.

(c)

A mixture of 1-ethyl-4-chloro-6-bromo-1H-pyrazolo[3,4-b]quinoline (6.5 g, 0.021 mol), cyclohexanemethylamine (5.46 g, 0.042 mol) and DMSO (20 ml) was heated at 110° C. overnight. The reaction mixture was cooled, poured into water and basified with $NH_4OH$. The mixture was extracted with $CH_2Cl_2$ (2×100 ml) and the combined $CH_2Cl_2$ extracts were washed with brine, then evaporated to about 20 ml. The solution was purified by column chromatography on silica gel eluting with ethyl acetate to afford 8.0 g (98.8%) of 1-ethyl-6-bromo-N-(cyclohexylmethyl)-1H-pyrazolo[3,4-b] quinolin- 4-amine, m.p. 158°–160° C.

(d)

Carbon monoxide was bubbled into a solution of bis-(triphenylphosphine)palladium II chloride (0.07 g, 0.1 mol), methanol (100 ml), triphenylphosphine (0.13 g, 0.5 mmol), sodium acetate (0.9 g, 11 mmol), 1-ethyl-6-bromo-N-(cyclohexylmethyl)-1H-pyrazolo[ 3,4-b]quinolin-4-amine (4 g, 10.3 mmol) and triethylamine (0.138 ml, 1 mmol) overnight while the solution was heated at 60°– 70° C. Additional bis(triphenylphosphine) palladium II chloride (0.07 g) was added and the mixture was heated until the reaction was complete. The catalyst was removed by filtration, the filtrate was evaporated and the residue was partitioned between $CH_2Cl_2$/water. The $CH_2Cl_2$ layer was separated and evaporated to afford 2.2 g of the free base, m.p. 115°–118° C. The free base (0.7 g) was dissolved in $CH_3CN$ and treated with 2N HCl. The salt which formed was collected by filtration and washed with ether to afford 0.47 g of 1-ethyl-6-methoxycarbonyl-N-(cyclohexylmethyl)-1H-pyrazolo[ 3,4-b] quinolin-4-amine.HCl, m.p. 27520 –277° C.

EXAMPLE 30

A mixture of 1-ethyl-6-methoxycarbonyl-N-(cyclohexylmethyl)- 1H-pyrazolo[3,4-b]quinoline-4-amine (1.4 g), ethanol (90 mL), KOH (2 g) and water (10 mL) was stirred at room temperature overnight. The reaction mixture was evaporated and the residue was partitioned between $CH_2Cl_2$ and water. The aqueous layer was separated, acidified with acetic acid and the solid which formed was collected by filtration and dried. The solid was recrystallized from hot acetic acid (50 mL) to afford 1.0 g of 1-ethyl- 6-carboxy-N-(cyclohexylmethyl)-1H-pyrazolo[3,4 -b]quinolin-4-amine. HOAc, m.p. 240° C.

EXAMPLE 31

A mixture 1-ethyl-6-bromo-N-(cyclohexylmethyl) -1H-pyrazolo [3,4-b]quinolin-4-amine (2.0 g, 5.17 mmol), DMF (20 mL), bis(triphenylphospine)palladium II chloride (0.05 g) and tri-n-butyl- 4-pyridyl stannane (2 g, 5.17 mmol) overnight, then at reflux overnight. The reaction mixture was poured into water and extracted with $CH_2Cl_2$ (3×30 mL). The $CH_2Cl_2$ extracts were combined, washed with water, dried over $Na_2SO_4$ and evaporated. The residue was purified by column chromatography on silica gel eluting with 20% ethyl acetate/hexane to 100% ethyl acetate to afford 1 g of the product as the free base. The free base was dissolved in $CH_2Cl_2$ (40–50 mL) and then was treated with methanesulfonic acid (20–30 mL). Ether was added to the mixture and the precipitate which formed was collected by filtration and washed with $CH_2Cl_2$ (10 mL). The solid was recrystallized from hot 2-propanol/methanol to afford 0.85 g of 1-ethyl-6-(4-pyridinyl-N-(cyclohexylmethyl)- 1H-pyrazolo [3,4-b]quinolin-4-amine.2 $CH_3SO_3H.1/6$ 2-propanol, m.p. 285° C.

EXAMPLE 32

1-Aminomethyl-1-cyclohexanol hydrochloride (1 g, 6.04 mmol) was dissolved in cold water and then $K_2CO_3$ and ether were added. The mixture was stirred and then the ether layer was separated and the aqueous layer was again extracted with ether. The ether layers were combined, dried over $MgSO_4$ and concentrated to afford 1-aminomethyl-1-cyclohexanol which was mixed with DMSO (3 mL) and 1-ethyl- 6-methoxy-1H-pyrazolo[3,4-b]quinoline (0.8 g, 3 mmol). The reaction mixture was stirred at 110° C. overnight and then was partitioned between water and CH$_2$Cl$_2$. The CH$_2$Cl$_2$ layer was separated, dried, filtered and evaporated. The residue was crystallized from CH$_2$Cl$_2$ and recrystallized from acetonitrile to afford 0.65 g of 1-ethyl-6-methoxy-N-[(1-hydroxycyclohexyl)methyl]- 1H-pyrazolo[3,4-b]quinolin-4-amine, m.p. 201–°203° C.

EXAMPLE 33

A mixture of DMSO (6 mL), chloroethylmorpholine hydrochloride (1.23 g, 6.6 mmol), 1-ethyl-6-hydroxy-N-(cyclohexylmethyl) - 1H-pyrazolo[3,4-b]quinolin-4-amine (2 g, 6.6 mmol) and KOH (1 g) was stirred at room temperature overnight. The reaction mixture was partitioned between CH$_2$Cl$_2$ and water and the CH$_2$Cl$_2$ layer was separated and evaporated. The residue was purified by column chromatography on silica gel eluting with 10% ethanol/ethyl acetate to afford the product as the free base. The free base was recrystallized from hot ethyl acetate/hexane to afford 0.425 g of 1-ethyl-6-[2-(4-morpholinyl)ethoxy]-N-(cyclohexylmethyl)-1H-pyrazolo[3,4-b]quinolin-4-amine, as a yellow powder, m.p. 176°–178° C.

EXAMPLE 34

A mixture of S(+)-1-cyclohexylethylamine (2.0 mL, 13.6 mmol), 1-ethyl-6-nitro-4-chloro-1H-pyrazolo[3,4-b]quinoline (2.76 g, 0.01 mol), DMSO (10 mL) and triethylamine (3 mL, 0.01 mol) was heated at 110° C. overnight. The reaction mixture was partitioned between CH$_2$Cl$_2$ and water and then the CH$_2$Cl$_2$ layer was separated and evaporated. The residue was crystallized from ethanol (40 mL) and collected by filtration. The solid was dissolved in warm methanol (100 mL) and then was treated with methanesulfonic acid. The methanol was evaporated to a volume of about 5 mL and the solid which crystallized from the solution was collected by filtration and washed with methanol and then ether to afford 1.71 g of 1-ethyl-6-nitro-N-[S(+)-1-(cyclohexyl) ethyl]-1H-pyrazolo[3,4-b]quinolin- 4-amine.CH$_3$SO$_3$H, m.p. 176°–178° C.

EXAMPLE 35

A mixture of R-(–)-1-cyclohexylethylamine (0.59 ml, 4 mmol), DMSO (2 ml) and 1-ethyl-6-nitro-4-chloro-1H-pyrazolo[3,4-b]quinoline (0.55 g, 2 mmol) was heated at 110° C. for 6 hours. The reaction mixture was cooled and then was partitioned between water (50 mL) and CH$_2$Cl$_2$ (50 mL). The CH$_2$Cl$_2$ layer was separated, washed with water, dried over MgSO$_4$, filtered and evaporated. The residue was purified by column chromatography on silica gel eluting with 50% ether/hexane/10% CH$_2$Cl$_2$ to afford the product as the free base. The free base was converted into the methanesulfonic acid salt following a procedure similar to that described in example 34 to afford 0.435 g of 1-ethyl-6-nitro-N-[R (–)-1(cyclohexyl)ethyl]- 1H-pyrazolo[3,4-b]quinolin-4amine.CH$_3$SO$_3$H.½ H$_2$O, m.p. 278°–279° C.

EXAMPLE 36

(a) and (b)

A mixture of 1-ethyl-6-nitro-4-chloro-1H-pyrazolo[3,4-b]quinoline (2.7 g, 17.8 mmol), triethylamine (3 mL, 0.02 mol), DMSO (15 mL) and 3-hydroxycyclohexylmethylamine (4.97 g, 18 mmol) was heated at 110° C. overnight. The reaction mixture was poured into ice-water (200 mL)/NH$_4$OH (10 mL) and the solid which formed was collected by filtration. The filtrate was then extracted with CH$_2$Cl$_2$ (2×100 mL). The solid was stirred and sonicated with CH$_2$Cl$_2$ (2×200 mL) and any solids which did not go into solution were collected by filtration. All of the above CH$_2$Cl$_2$ filtrates and extracts were combined, washed with water and evaporated. The residue was slurried with ethyl acetate (10–15 mL)/ether (20 mL) and a red colored solid was collected by filtration and washed with ether. The solid was purified by column chromatography (2×) on silica gel (note that the solid was preloaded onto 50–100 g of silica gel) eluting with 40% THF/cyclohexane and each of the diastereomers which was isolated was dissolved in hot THF, filtered and the solvent was evaporated. Each of the residues was slurried with ethanol (5 mL), filtered and dried to afford 0.69 g of 1-ethyl-6-nitro-N-(3-hydroxycyclohexylmethyl)-1H-pyrazolo[3,4-b]quinolin- 4-amine (the RS,SR diastereomer which is labelled as Example 36(a)), m.p. 236°–238° C. and 2.23 g of 1-ethyl-6-nitro-N-(3-hydroxycyclohexylmethyl)-1H-pyrazolo[3,4-b]quinolin-4-amine (the RR,SS diastereomer which is labelled as Example 36(b)), m.p. 247°–248° C.

EXAMPLE 37

(a)

A solution of 2-chloro-5-(methylthio)benzoic acid (25 g, 123 mmol) dissolved in methanol (500 ml) was cooled to 0°–5° C. and then OXONE® (227.6 g, 370 mol) in water (500 ml) was added. The reaction mixture was stirred for 30 minutes at 0°–5° C. and then at room temperature for 4 hours. The reaction mixture was diluted with water, extracted with CHCl$_3$ (3×200 ml) and the CHCl$_3$ extracts were combined, washed with water, then brine and then were dried over MgSO$_4$, filtered and evaporated to afford 5.13 g of 2-chloro-5-(methylsulfonyl)benzoic acid, m.p. 187°–188° C.

(b)

A mixture of 2-chloro-5-(methylsulfonyl)benzoic acid (5.0 g, 21.4 mmol), 5-amino-1-ethylpyrazole (2.4 g, 21.4 mmol), DMF (50 ml), Cu(OAc)$_2$ (0.5 g) and K$_2$CO$_3$ (2.76 g, 20 mmol) was heated at reflux overnight. The reaction mixture was poured into water, acidified with acetic acid and extracted with CH$_2$Cl$_2$. The CH$_2$Cl$_2$ layer was evaporated to afford N-(1-ethylpyrazol-5-yl)-5-(methylsulfonyl)anthranilic acid.

(c)

A mixture of N-(1-ethylpyrazol-5-yl) -5-(methylsulfonyl) anthranilic acid of example 37 (b) and POCl$_3$ (50 ml) was heated at 110° C. for 16 hours. The reaction mixture was poured into ice-water, neutralized with NH$_4$OH and extracted with CH$_2$Cl$_2$. The CH$_2$Cl$_2$ layer was evaporated and the residue was purified by column chromatography on silica gel eluting with 50% ether/CH$_2$Cl$_2$ to afford 1.1 g of 1-ethyl-4-chloro-6-(methylsulfonyl)-1H-pyrazolo[3,4-b] quinoline, m.p. 158°–160° C.

(d)

A mixture of 1-ethyl-4-chloro-6-(methylsulfonyl)-1H-pyrazolo[ 3,4-b]quinoline (1.1 g, 3.56 mmol), DMSO (3 ml) and S(+)-1-cyclohexylethylamine (1.06 ml, 7.12 mmol) was heated at 110° C. overnight. The reaction mixture was partitioned between water (25 ml) and CH$_2$Cl$_2$ (25 ml), the layers were separated and the aqueous layer was extracted with CH$_2$Cl$_2$ (25 ml). The CH$_2$Cl$_2$ extracts were combined, washed with water, dried over MgSO$_4$, and evaporated. The residue was purified by column chromatography on silica gel eluting with 50% CH$_2$Cl$_2$/30% hexane/20% ethyl acetate to afford 1-ethyl-6-(methylsulfonyl)-N-[S(+)-1-(cyclohexyl)ethyl]-1H-pyrazolo[ 3,4-b]quinolin-4-amine, [α]$^{25}$D=+119.6° (C=1% CHCl$_3$).

EXAMPLE 38

(a)+(b)

A mixture of 1-benzyl-4-chloro-1H-pyrazolo[3,4-b]quinoline (5.86 g, 0.02 mol), DMSO (20 ml) and S(+)-1-cyclohexylethylamine (5.1 g, 0.04 mol) was heated at 110°–120° C. for 18 hours. The reaction mixture was cooled to room temperature, then was poured into ice-water. The resulting solid was collected by filtration, washed with water and dried to give 7.8 g of crude product which was purified by column chromatography on silca gel eluting with CH$_2$Cl$_2$/ether (9/1) to afford 6.1 g (79%) of 1-benzyl-N-[S(+)-1(cyclohexyl)ethyl]- 1H-pyrazolo[3,4-b]quinolin-4-amine (labelled as Example 38(a). The free base (0.6 g) was dissolved in CH$_2$Cl$_2$ and treated with ethereal HCl and the resulting salt was collected by filtration and dried to afford 0.5 g of 1-benzyl-N-[S(+)-1-(cyclohexyl)ethyl]- 1H-pyrazolo[3,4-b]quinolin-4-amine.HCl (labelled as example 38(b)), as a white solid, m.p. 260°–262° C.

EXAMPLE 39

A mixture of 1-ethyl-4-chloro-1H-pyrazolo[3,4-b]quinoline (1 g), DMSO (3 ml) and S(+)-1-cyclohexylethylamine (1 ml) was heated at 110° C. overnight. The reaction mixture was cooled, then was partitioned between water (25 ml) and CH$_2$Cl$_2$ (25 L). The layers were separated and the CH$_2$Cl$_2$ layer was evaporated. The residue was purified by column chromatography on silica gel eluting with 70% ethyl acetate/hexane to afford an oil which was crystallized from hexane and recrystallized from ether/hexane to afford 0.65 g of 1-ethyl-N-[S(+)-1-(cyclohexyl)ethyl]-1H-pyrazolo[ 3,4-b]quinolin-4-amine, m.p. 135°–136°, [α]$^{25}$D=+66.0 (C=1 % CHCl$_3$ ).

EXAMPLE 40

(a)

A mixture of D-(–)-alpha-aminophenylacetic acid ethyl ester hydrochloride (10.8 g, 0.05 mol), ethanol (50 ml) and rhodium on alumina (0.5 g) was hydrogenated on a Parr apparatus at 50 psi and 40° C. for 5 hours. Additional catalyst (1 g) was added and the mixture was hydrogentated at 50 psi and 40° C. for one day. The catalyst was filtered off, the filtrate was evaporated and the residue was washed with ether to afford R-(–)-alpha-aminocyclohexyl acetic acid ethyl ester hydrochloride, as a white solid, m.p. 179°–180° C., [α]$^{25}$D=–20.1° (C=1% CHCl$_3$).

(b)

A mixture of R-(–)-alpha-aminocyclohexylacetic acid ethyl ester hydrochloride (3.0 g, 13.6 mmol), LAH (30 g) and THF (50 mL) was stirred in an ice bath for 1 hour, then at 60° C. for 3 hours and finally at reflux for 0.5 hours. The reaction mixture was quenched with water (3 mL), 10% NaOH (3 mL) and then water (9 mL). The solids which formed were collected by filtration and washed with THF and ether. The filtrate was dried over MgSO$_4$, filtered and concentrated in vacuo to afford, after recrystallization from hot hexane, 1.273 g of R-(–)-2-(cyclohexyl)-2-aminoethanol, m.p. 86°–87° C., [α]$^{25}$D=–14.3° (c=1% CHCl$_3$).

(c)

A mixture of 1-ethyl-4-chloro-6-nitro-1H-pyrazolo[3,4-b]quinoline (1.0 g), R-(–)-2-(cyclohexyl)-2-aminoethanol (1.0 g) and DMSO was heated at 110° C. overnight. The reaction mixture was partitioned between CH$_2$Cl$_2$ and water, and then the CH$_2$Cl$_2$ layer was separated and evaporated. The residue was purified by column chromatography on silica gel eluting with ethyl acetate/hexane/CH$_2$Cl$_2$, and the resulting product was crystallized ethanol and then recrystallized from ethanol to afford 0.66 g of 1-ethyl-6-nitro-N-[R-(–)-1-(cyclohexyl)ethanol]-1H-pyrazolo[3,4-b]quinolin-4-amine, m.p. 249°–250° C.

EXAMPLE 41

(a)

A mixture of S(+)-1-cyclohexylethylamine (0.9 g, 7 mmol), DMSO (5 ml) and 1-ethyl-6-bromo-4-chloro-1H-pyrazolo[3,4-b]quinoline (1.1 g, 3.5 mmol) was heated at 110°–120° C. for 18 hours. The reaction mixture was cooled to room temperature, then was poured into ice-water. The product was isolated by filtration and purified by column chromatography on silica gel eluting with CH$_2$Cl$_2$/ether (8/2) to afford 0.89 g (62%) of 1-ethyl-6-bromo-N-[S(+)-(1-cyclohexyl)ethyl]-1H-pyrazolo[3,4-b]quinolin.4-amine.

(b)+(c)

A suspension of 1-ethyl-6-bromo-N-[S(+)-(1-cyclohexyl)ethyl- 1H-pyrazolo[3,4-b]quinolin-4-amine (0.88 g, 2.2 mmol), DMF (10 ml) and copper (I) cyanide (0.22 g, 2.5 mmol) was refluxed for 24 hours. Additional CuCN (0.22 g) was added and the mixture was refluxed for about 2 days. The reaction mixture was filtered and the filtrate was evaporated to dryness. The residue was dissolved in CH$_2$Cl$_2$, washed with NH$_4$OH and the CH$_2$Cl$_2$ layer was dried over MgSO$_4$, and evaporated to dryness. The residue was purified by column chromatography on silica gel eluting with CH$_2$Cl$_2$/ether (9/1) to afford 0.48 g (63%) of 1-ethyl-6-bromo-N-[S(+)-( 1-cyclohexyl)ethyl]-1H-pyrazolo[3,4-b]quinolin-4-amine (labeled as Example 41(b)). The free base was dissolved in ether/CH$_2$Cl$_2$ and the ethereal HCl was added. The resulting solid was collected by filtration and recrystallized from isopropanol/ether to afford 0.35 g of 1-ethyl-6-cyano-N-[S(+)-(1-cyclohexyl)ethyl]- 1H-pyrazolo[3,4-b]quinolin-4-amine.HCl (labeled Example 41 (c)), as a yellow solid, m.p. 298°–300° C.

EXAMPLE 42

(a)

A mixture of 5-amino-1-ethylpyrazole (5.0 g, 45 mmol), 2-bromo- 4,5-dimethoxybenzoic acid (11.76 g, 45 mmol), K$_2$CO$_3$ (6.21 g, 45 mmol), Cu(OAc)$_2$ (0.8 g, 400 mmol) and DMF (125 ml) was refluxed overnight. The reaction mixture was cooled, poured into water and acidified with acetic acid. The resulting solid was collected by filtration and dried to afford 12.8 g (97%) of N-(1-ethylpyrazol-5-yl)-4,5-dimethoxyanthranilic acid.

(b)

A mixture of N-(1-ethylpyrazol-5-yl)-4,5-dimethoxy anthranilic acid (12.8 g, 44 mmol) and POCl$_3$ (75 ml) was refluxed for 8 hours. The reaction mixture was cooled to room temperature, poured into ice-water and neutralized with concentrated NH$_4$OH. The mixture was extracted with CH$_2$Cl$_2$ and the CH$_2$Cl$_2$ layer was dried over MgSO$_4$ and evaporated to dryness. The residue was purified by column chromatography on silica gel eluting with CH$_2$Cl$_2$/ether (9/1) to afford 8.0 g (62%) of 1-ethyl-4-chloro-6,7-dimethoxy-1H-pyrazolo[3,4-b]quinoline.

(c)

A mixture of 1-ethyl-4-chloro-6,7-dimethoxy-1H-pyrazolo[-3,4-b]quinoline (8.0 g, 27.44 mmol), DMSO (20 ml) and S(+)-1-cyclohexylethylamine (8 ml, 54.88 mmol) was heated at 100°–110° C. overnight, then at 130°–140° C. for 48 hours. The reaction mixture was cooled to room temperature and then was poured into ice-water. The resulting product was collected by filtration and purified by column chromatography on silica gel eluting with CH$_2$Cl$_2$/ether (4/1) to afford 9.3 g of the product as the free base. The free base (1.0 g) was dissolved in CH$_2$Cl$_2$ and treated with ethereal HCl to afford a gummy salt which crystallized on standing. The hydrochloride salt was recrystallized from isopropanol/ether to afford 0.7 g of 1-ethyl-6,7-dimethoxy-N-[S (+)-1-(cyclohexyl)ethyl-1H-pyrazolo[3,4-b]quinolin-4-amine.HCl.¼ hydrate, m.p. 185°–187° C. (dec.), [α]$^{25}$D= +123° (C=1% methanol).

EXAMPLE 43

A mixture of 1-ethyl-6-bromo-N-[S(+)-1-(cyclohexyl)ethyl]-1H-pyrazolo[3,4-b]quinolin-4-amine (10 g, 2.5 mmol) and imidazole (0.51 g, 7.5 mmol) was heated at 120°–130° C. for 6 hours, then at 170°–180° C. overnight. N-Methyl-2-pyrrolidinone (2 ml) was added and the mixture was heated at 170°–180° C. for 2 hours. Starting material was still present so K$_2$CO$_3$ (0.5 g, 3.6 mmol) and a catalytic amount of Cu(OAc)$_2$ were added and the mixture was heated at 160°–170° C. for about 2 days. The reaction mixture was cooled to room temperature and then was poured into ice-water. The resulting solid was collected by filtration, washed with water and dried. The solid residue was dissolved in methanol and treated with an equivalent amount of methanesulfonic acid. A gummy solid formed which was dissolved in CH$_2$Cl$_2$ and neutralized with concentrated NH$_4$OH. The CH$_2$Cl$_2$ layer was separated, dried over MgSO$_4$ and evaporated to dryness. The solid residue was recrystallized from CH$_2$Cl$_2$/ethyl acetate to afford 0.51 g (52%) of 1-ethyl-6-(1-imidazolyl)-N-[S(+)- 1-(cyclohexyl)ethyl]-1H-pyrazolo[3,4-b]quinolin- 4-amine, as a yellow solid, m.p. 256°–258° C.

EXAMPLE 44

(a)

A mixture of 5-amino-1-ethylpyrazole (33.7 g, 0.3 mol), 2,5-dibromobenzoic acid (84 g, 0.3 mol), K$_2$CO$_3$ (41.4 g, 0.3 mol), Cu(OAc)$_2$ (1 g) and DMF (500 mL) was refluxed overnight. The reaction mixture was poured into ice-water (4 L) and was then acidified with acetic acid. The solid which formed was collected by filtration and dried to afford 35 g of a mixture of N-(1-ethylpyrazol- 5-yl)-3-bromoanthranilic acid and N-(1-ethylpyrazol-5-yl)-5-bromoanthranilic acid.

(b) and (c)

A mixture of N- (1-ethylpyrazol-5-yl)-3-bromoanthranilic acid and N-(1-ethylpyrazol-5-yl)-5-bromoanthranilic acid (34.8 g, 0.11 mol) and POCl$_3$ (100 mL) was heated at reflux for 8 hours. The reaction mixture was cooled to room temperature and then was poured into ice-water and neutralized with concentrated NH$_4$OH. The mixture was extracted with CH$_2$Cl$_2$ and the CH$_2$Cl$_2$ layer was dried over MgSO$_4$ and evaporated to dryness. The residue was purified by column chromatography on silica gel eluting with CH$_2$Cl$_2$/ether (9/1) to afford 2.7 g of 1-ethyl-4-chloro-8-bromo-1H-pyrazolo[3,4-b]quinoline (labelled as Example 44 (b)) and 22.5 g (64%) of 1-ethyl-4-chloro-6-bromo-1H-pyrazolo[3,4-b]quinoline (labelled as Example 44 (c)).

(d)

A mixture of 1-ethyl-4-chloro-8-bromo-1H-pyrazolo[3,4-b]quinoline (2.0 g, 6.44 mmol), DMSO (5 mL) and cyclohexylmethylamine (1.46 g, 12.9 mmol) was heated at 80°–90° C. for 3 hours. The reaction mixture was cooled to room temperature and then was poured into water. The resulting solid was collected by filtration, washed with water and evaporated. The residue was purified by column chromatography on silica gel eluting with CH$_2$Cl$_2$/ether (9/1) to afford 2.0 g (80%) of 1-ethyl-8-bromo-N-(cyclohexylmethyl)-1H-pyrazolo[3,4-b]quinolin-4-amine, as a yellow solid, m.p. 160°–162° C.

EXAMPLE 45

(a)

A mixture of 2-chloro-5-(fluorosulfonyl)benzoic acid (11.93 g, 0.05 mol), diethylamine (10.97 g, 0.15 mol) and 1,2-dichloroethane (100 mL) was refluxed for 8 hours. The reaction mixture was evaporated and the residue was dissolved in ethyl acetate. A solid was collected by filtration and the filtrate was evaporated to dryness to afford 15.5 g of 2-chloro-5-diethylaminosulfonyl)benzoic acid.

(b)

A mixture of 5-amino-1-isopropylpyrazole (6.43 g, 0.051 mol), 2-chloro-5-(diethylaminosulfonyl)benzoic acid (15.0 g, 0.051 mol), K$_2$CO$_3$(7.04 g, 0.051 mol), Cu(OAc)$_2$ (1.0 g) and DMF (100 mL) was refluxed for 24 hours. The reaction mixture was concentrated in vacuo and the residue was poured into water and neutralized with acetic acid. The mixture was extracted with CH$_2$Cl$_2$ and the CH$_2$Cl$_2$ layer was dried over MgSO$_4$ and evaporated to afford 12.1 g of N-(1-isopropylpyrazol-5-yl)-5-(diethylaminosulfonyl) anthranilic acid.

(c)

A mixture of N-(1-isopropylpyrazol-5-yl)-5-(diethylaminosulfonyl) anthranilic acid (12.0 g, 0.031 mol) and POCl$_3$ (80 mL) was refluxed for 6 hours. The reaction mixture was cooled to room temperature and then was poured into ice-water and neutralized with concentrated NH$_4$OH. The mixture was extracted with CH$_2$Cl$_2$ and the CH$_2$Cl$_2$ layer was dried over MgSO$_4$ and evaporated to dryness. The residue was purified by column chromatography on silica gel eluting with CH$_2$Cl$_2$/ether (9/1) to afford 10 g of crude 1-isopropyl- 6-(diethylaminosulfonyl)-4-chloro-1H-pyrazolo[3,4-b]quinoline.

(d)

A mixture of 1-isopropyl-6-(diethylaminosulfonyl)-4-chloro- 1H-pyrazolo[3,4-b]quinoline (1.0 g, 2.63 mmol), DMSO (2.5 mL) and cyclohexylmethylamine (0.6 g, 5.3 mmol) was heated at 120°–130° C. for 18 hours. The reaction mixture was cooled to room temperature and then was poured into ice-water. The mixture was extracted with $CH_2Cl_2$ and the $CH_2Cl_2$ layer was dried over $MgSO_4$ and evaporated to dryness. The residue was purified by column chromatography on silica gel eluting with $CH_2Cl_2$/ether (9/1) to afford 0.13 g of the product as the free base. The free base was dissolved in $CH_2Cl_2$ and was treated with ethereal.HCl. The solvent was decanted and the residue was treated with ether to afford, after recrystallization from $CH_2Cl_2$/ether, 0.11 g of 1-isopropyl-6-(diethylaminosulfonyl)-N-(cyclohexylmethyl)-1H-pyrazolo[3,4 -b]quinolin-4-amine.HCl, as an off-white solid, m.p. 170°–172° C. (dec.).

EXAMPLE 46

A mixture of 1-ethyl-4-chloro-6-bromo-1H-pyrazolo[3,4-b]quinolin- 4-amine (15.53 g, 0.05 mol), S(+)-1-cyclohexylethylamine (12.73 g, 0.1 mol) and DMSO (20 mL) was heated at 12020–130° C. for 20 hours. The reaction mixture was cooled to room temperature and then was poured into ice-water. The resulting solid was collected by filtration, washed with water and dried to afford 19.6 g of crude product. The crude product (1.5 g) was purified by column chromatography on silica gel eluting with $CH_2Cl_2$/ether (9/1), followed by recrystallization from ether/hexane to afford 1.0 g of 1-ethyl-6-bromo-N-[S(+)-1-(cyclohexyl)ethyl]-1H-pyrazolo[3,4-b]quinolin-4-amine, m.p. 148°–150° C., $[\alpha]^{25}D=+83.3°$ (C=1% methanol).

EXAMPLE 47

(a)

A mixture of 1-ethyl-6-bromo-N-[S (+)-1-(cyclohexyl)ethyl]-1H-pyrazolo[3,4-b]quinolin-4-amine (5.0 g, 12.47 mmol), CuCN (3.35 g, 37.41 mmol), NaCN (1.83 g, 37.41. mmol) and DMF (35 mL) was refluxed for about 3 days. The reaction mixture was evaporated to dryness and the residue was partitioned between $CH_2Cl_2$ and concentrated NH4OH. The $CH_2Cl_2$ layer was separated, washed with water, dried over $MgSO_4$ and concentrated in vacuo to afford 4.5 g of 1-ethyl-6-cyano-N-[S(+)-1-(cyclohexyl)ethyl]- 1H-pyrazolo[3,4-b]quinolin-4-amine.

(b)

To a solution of sodium methoxide (prepared from methanol (80 mL) and sodium metal (0.6 g, 26 mmol)) was added hydroxylamine hydrochloride and the mixture was stirred at room temperature for 1.5 hours. The reaction mixture was filtered and the filtrate was added to 1-ethyl-6-cyano-N-[S(+)-1-(cyclohexyl)ethyl]-1H-pyrazolo[ 3,4-b]quinolin-4-amine (4.5 g, 13 mmol). The resulting mixture was refluxed for 48 hours and then the solvent was evaporated to dryness to afford 4.7 g of 1-ethyl-6-[C(=NOH) $NH_2$]-N-[S(+)-1(cyclohexyl)ethyl]- 1H-pyrazolo[3,4-b]quinolin-4-amine.

(c)

A mixture of 1-ethyl-6-[C(=NOH)$NH_2$]-N-[S(+)-1-(cyclohexyl)ethyl]- 1H-pyrazolo[3,4-b]quinolin-4-amine (4.7 g, 12.37 mmol) and acetic anhydride (20 mL) was heated at 120° C. for 2 hours. The solvent was removed in vacuo and water was added to the residue. The mixture was neutralized with saturated $K_2CO_3$ and then was extracted with ethyl acetate. The organic layer was dried over $MgSO_4$ and evaporated. The residue was purified by column chromatography on silica gel eluting with $CH_2Cl_2$/ether (9/1) to afford, after recrystallization from ether/hexane, 0.6 g of 1-ethyl- 6-[5-methyl-3-(1,2,4-oxadiazolyl)-N-[S(+)-1-(cyclohexyl)ethyl]- 1H-pyrazolo[3,4-b]quinolin-4-amine .¼ $H_2O$, as a yellow solid, m.p. 113°–115° C.

EXAMPLE 48

(a)

A mixture of 2-chloro-5-(methylthio)benzoic acid (8.8 g, 0.043 mol), DMF (100 mL), 5-amino-1-ethylpyrazole (4.8 g, 0.043 mol), $K_2CO_3$ (5.94 g, 0.043 mol) and Cu(OAc)$_2$ (0.5 g ) was refluxed overnight. The reaction mixture was cooled to room temperature, poured into water and acidified with acetic acid to a pH of about 4–5. The mixture was extracted with $CH_2Cl_2$ and then the $CH_2Cl_2$ layer was evaporated to afford 4.5 g of N-(1-ethylpyrazol-5-yl)-5-(methylthio)anthranilic acid.

(b)

A mixture of N-(1-ethylpyrazol-5-yl)-5-(methylthio) anthranilic acid (4.5 g) and $POCl_3$ (20 mL) was refluxed overnight. The reaction mixture was poured into water, then ice was added. The mixture was extracted with $CH_2Cl_2$ and then the $CH_2Cl_2$ layer was evaporated. The residue was purified by column chromatography on silica gel eluting with 50% ethyl acetate/hexane to afford 2.4 g of 1-ethyl-4-chloro-6-(methylthio)-1H-pyrazolo[3,4-b]quinoline, m.p. 120°–121° C.

(c)

To a solution of 1-ethyl-4-chloro-6-(methylthio)-1H-pyrazolo[ 3, 4-b]quinoline (2.4 g, 8.7 mmol) in $CHCl_3$ (50 mL) at −40° C. was added m-chloroperoxybenzoic acid (2.75 g, 8.7 mmol). The reaction mixture was slowly warmed to 0° C. and then saturated $NaHCO_3$ (10 mL) was added. The reaction mixture was partitioned between water (20 mL) and $CH_2Cl_2$ (20 mL), the layers were separated and then the aqueous layer was extracted with $CH_2Cl_2$ (20 ml). The $CH_2Cl_2$ extracts were combined, dried over $MgSO_4$ and evaporated. The residue was purified by column chromatography on silica gel eluting with 50% ether/hexane, then 25% ethyl acetate/25% hexane/50% ether and finally ethyl acetate (100%) to afford 2.4 g of 1-ethyl-4-chloro-6-(methylsulfinyl)-1H-pyrazolo[ 3,4-b]quinoline.

(d) and (e)

A mixture 1-ethyl-4-chloro-6-(methylsulfinyl)-1H-pyrazolo[ 3,4-b]quinoline (2.0 g, 0.014 mol), DMSO (5 mL) and S(+)-1cyclohexylethylamine (4.2 mL, 0.028 mol) was heated at 110° C. overnight. The reaction mixture was cooled, then was partitioned between $CH_2Cl_2$ (30 mL) and water (30 mL) containing NH4OH (5 mL). The layers were separated and the aqueous layer was extracted with $CH_2Cl_2$. The $CH_2Cl_2$ extracts were combined and evaporated to dryness and the residue was passed through a silica gel column eluting with ethyl acetate to afford the product as a mixture of diastereomers. The diasteromers were separated by repeated recrystallizations from hot ethyl acetate to afford 1-ethyl-6-(methylsulfinyl)-N-[S(+)- 1-(cyclohexyl)ethyl]-

1H-pyrazolo[3,4-b]quinolin- 4-amine [one diasteromer of which is labelled as Example 48(d), m p 195°–196° C. $[\alpha]^{23.8}D=+47.9°$ (C=20 mg/2 mL of $CDCl_3$) and the other diasteromer of which is labelled as Example 48 (e), m.p. 235°–236° C. $[+]^{23.8}D=+217.6°$ (C=20 mg/2 mL of $CDCl_3$)].

EXAMPLE 49

A mixture of 1-ethyl-4-chloro-6-(methylsulfinyl)-1H-pyrazolo[ 3,4-b]quinoline (0.4 g, 2.8 mmol), DMSO (1.5 mL) and cyclohexylmethylamine (0.73 mL, 5.6 mmol) was heated at 110° C. over night. The reaction mixture was cooled to room temperature, then was partitioned between $CHCl_3$ (20 mL) and water (20 mL) containing $NH_4OH$ (3 mL). The layers were separated, the aqueous layer was extracted with $CH_2Cl_2$ (10 mL) and the organic layers were combined dried over $MgSO_4$ and evaporated. The residue was purified by column chromatography on silica gel eluting with ethyl acetate, followed by recrystallization from ethyl acetate (2×) to afford 0.115 g of 1-ethyl-6-(methylsulfinyl)-N-(cyclohexylmethyl)-1H-pyrazolo[ 3,4-b]quinolin-4-amine, m.p. 186°–187° C.

EXAMPLE 50

A mixture of 1-ethyl-6-bromo-N-[S(+)-1-(cyclohexyl)ethyl]-1H-pyrazolo[3,4-b]quinolin-4-amine (1.0 g, 2.5 mmol), 4-methylpyrazole (1.0 g, 12.18 mmol), $K_2CO_3$ (1.0 g, 7.2 mmol), $Cu(OAc)_2$ (catalytic amount) and N-methyl-2-pyrrolidinone (3 mL) was heated at about 160°–170° C. for about 2 days. The reaction mixture was cooled to room temperature, $CH_2Cl_2$ was added and then the mixture was poured into ice-water. The $CH_2Cl_2$ layer was separated, dried over $MgSO_4$ and evaporated to dryness. The residue was purified by column chromatography on silica gel eluting with $CH_2Cl_2$/ether (9/1) to afford 1.0 g of the product as the free base. The free base was dissolved in ether, treated with ethereal.HCl and then was triturated with ether. The resulting salt was collected by filtration, washed with ether and dried to afford, after recrystallization from $CH_2Cl_2$/ether (2×), 0.48 g of 1-ethyl-6-(4-methyl-1-pyrazolyl)-N-[S(+)-1-(cyclohexyl)ethyl]-1H-pyrazolo[ 3,4-b]quinolin-4-amine-.HCl, m.p. 310°–312° C.

EXAMPLE 51

A mixture of 1-ethyl-6,7-dimethoxy-N-[S(+)-1-(cyclohexyl)ethyl]- 1H-pyrazolo[3,4-b]quinolin-4-amine (1.0 g, 2.6 mmol) and pyridine hydrochloride (1.0 g, 8.65 mmol) was heated for four hours and then was cooled to room temperature. Water was added to the reaction mixture and the resulting solid was collected by filtration, washed with water and dissolved in 5N NaOH. The aqueous layer was neutralized with acetic acid and the resulting solid was collected by filtration, washed with water and dried to afford 0.6 6 g of crude product. The crude product was recrystallized from ethanol to afford 0.55 g of 1-ethyl-6,7-dimethoxy-N-[S(+)- 1-(cyclohexyl)ethyl]-1H-pyrazolo[3,4-b]quinolin-4-amine.¾ $H_2O$, m.p. >250° C.

EXAMPLE 52

A mixture 1-ethyl-6-bromo-N-[S (+)-1-(cyclohexyl)ethyl]-1H-pyrazolo[ 3,4-b]quinolin-4-amine (1.0 g, 2.5 mmol), pyrazole (0.83 g, 12.18 mmol), $K_2CO_3$ (1.0 g, 7.2 mmol), $Cu(OAc)_2$ (catalytic amount) and N-methyl-2-pyrrolidinone (3 mL) was heated at about 160°–170° C. for about 4 days. The reaction mixture was cooled to room temperature and then was poured into an excess of ice-water. The resulting solid was collected by filtration, washed with water and dried to afford 1.3 g of crude product. The crude product was purified by column chromatography on silica gel eluting with $CH_2Cl_2$/ether (9/1) to afford 0.56 g (58%) of the product as the free base. The free base was dissolved in ether and treated with ethereal.HCl. The resulting salt was collected by filtration, washed with ether, dried and then was recrystallized from acetonitrile to afford 0.47 g of 1-ethyl-6-(1-pyrazolyl)-N-[S(+)-1-(cyclohexyl)ethyl]-1H-pyrazolo[3,4-b]quinolin-4-amine .HCl, m.p. 278°–280° C., $[\alpha]^{25}D=+150°$ (C=1% methanol).

EXAMPLE 53

(a)

A mixture of 5-amino-1-ethylpyrazole (0.56 g, 5 mmol), 2-chloro-5-(trifluoromethylsulfonyl)benzoic acid (1.4 g, 4.9 mmol), $K_2CO_3$ (0.69 g, 5 mmol), $Cu(OAc)^2$ (0.1 g) and DMF (10mL) was refluxed for 4 hours and then was cooled to room temperature and was allowed to stand for about 3 days. Water was added to the reaction mixture and then the solution was acidified with acetic acid to a pH of about 5. The mixture was extracted with $CH_2Cl_2$ and then the $CH_2Cl_2$ layer was evaporated to afford N-(1-ethylpyrazol-5-yl)-5- trifluoromethylsulfonyl)anthranilic acid.

(b)

A mixture of N-(1-ethylpyrazol-5-yl) -5-(trifluoromethylsulfonyl)anthranilic acid and $POCl_3$ (30 mL) was heated on a steam bath overnight. The reaction mixture was poured onto ice-water and then was neutralized with $NH_4OH$. The resulting solid was collected by filtration, washed with water, dissolved in $CH_2Cl_2$, dried over $MgSO_4$, filtered and stripped. The residue was purified by column chromatography on silica gel eluting with 10% ethyl acetate/hexane to afford 1.0 g of 1-ethyl-4-chloro-6-(trifluoromethylsulfonyl)-1H-pyrazolo[3,4-b]quinoline.

(c)

A mixture of 1-ethyl-4-chloro-6-(trifluoromethylsulfonyl)- 1H-pyrazolo[3,4-b]quinoline (1.0 g, 3.1 mmol), DMSO and S(+)-1-cyclohexylethylamine (0.79 g, 6.2 mmol) was heated at 110° C. overnight. The reaction mixture was cooled to room temperature and then was partitioned between $CH_2Cl_2$ (50 mL) and aqueous $NH_4OH$. The $CH_2Cl_2$ layer was washed with water, then brine and then the solvent was evaporated. The residue was purified by column chromatography on silica gel eluting with 50% ethyl acetate/hexane to afford an oil which was treated with ethereal.HCl to afford 285 mg of 1-ethyl-6-(trifluoromethylsulfonyl)-N-[S (+)- 1-(cyclohexyl)ethyl]-1H-pyrazolo[ 3,4-b]quinolin-4-amine.HCl, m.p. 175°–185° C., $[\alpha]^{25}D=+101°$ (C=1% $CHCl_3$).

EXAMPLE 54

A mixture of 1-ethyl-4-chloro-6-nitro-1H-pyrazolo[3,4-b] quinoline (0.84 g, 3 mmol), DMSO (2 mL), triethylamine (0.42 mL), 3 mmol) and S(+)-1-cyclohexylpropylamine (0.43 g, 3 mmol) was heated at 110° C. for 5 hours. The reaction mixture was cooled to room temperature, and then was partitioned between water (40 mL) containing $NH_4OH$ (5 mL) and $CH_2Cl_2$ (50 mL). The layers were separated and the aqueous layer was extracted with $CH_2Cl_2$ (2×50 mL). The $CH_2Cl_2$ extracts were combined, washed with water (20 mL) and then evaporated. The residue was purified by column chromatography on silica gel eluting with ethyl acetate to afford the product as the free base. The free base was dissolved in ether, treated with ethereal.HCl and the solution was evaporated. The residue was crystallized from $CH_2Cl_2$/ether to afford 745 mg of 1-ethyl-6-nitro-N-[S(+)-1-(cyclohexyl)propyl]-1H-pyrazolo[3,4-b]quinolin-4-amine.HCl.

EXAMPLE 55

A mixture of 1-ethyl-6-bromo-N-[S(+)-1-(cyclohexyl)ethyl]-1H-pyrazolo[3,4-b]quinolin-4-amine (4.01 g, 10 mmol), DMF (10 mL), $CH_2$=CHSn(n-butyl)$_3$ (3.5 g, 11 mmol) and $(Ph_3P)_2PdCl_2$ (100 mg, 0.14 mmol) was refluxed for 4 days. The reaction mixture was evaporated to dryness and then the residue was dissolved in $CH_2Cl_2$ and washed with water and then a 10% NaF solution. The $CH_2Cl_2$ layer was dried over $MgSO_4$, the solvent was removed and the residue was purified by column chromatography on silica gel eluting with 20% ethyl acetate/hexane to afford, after recrystallization from ether/hexane, 0.21 g of 1-ethyl-6-(ethenyl)-N-[S(+)-1(cyclohexyl) ethyl]-1H-pyrazolo[3,4-b]quinolin-4-amine .¼ $H_2O$, m.p. 133°–135° C.

Biological Test Results

In standard biological test procedures, the compounds of Formula I have been found to possess c-GMP-PDE V (formerly named as c-GMP-PDE I) inhibitory activity and are thus useful in the treatment of heart failure and hypertension. The compounds of Formula I, in combination with nitrates, have also been found to be useful in reversing or reducing nitrate-induced tolerance and thus would be useful in the treatment of angina pectoris, congestive heart disease and myocardial infarction.

Multiple isozymic forms of cyclic nucleotide phosphodiesterase (PDE) have been identified in mammalian cells. These isozymes hydrolyze cyclic adenosine monophosphate (cAMP) and/or cyclic guanosine monophosphate (cGMP) to the presumably biologically inactive 5'-nucleotide phosphates. Elevation of intracellular cGMP in vascular smooth muscle triggers a cascade of events that leads to a reduction in muscle tone while elevations in renal tubule cell cGMP stimulates natriuresis and diuresis. Vascular smooth muscle and renal cells contain a phosphodiesterase isozyme that has a low Km (1 µM) for the hydrolysis of cGMP. This isozyme has been referred to as the cGMP-PDE or cGMP-PDE V (formerly was named as cGMP-PDE I since it eluted from an anion-exchange sepharose resin in the first peak of PDE activity at a sodium acetate concentration between 150–200 mM). Thus inhibition of the cGMP-PDE isozyme is a viable subcellular mechanism by which increases in cGMP can produce a reduction in total peripheral resistance and a stimulation of natriuresis and diuresis. The development of cGMP-PDE inhibitors represents an approach for the discovery of agents useful for treating heart failure and hypertension. For example, compounds having high inhibitory potency for the cGMP-PDE are expected to lower blood pressure and induce natriuresis and diuresis.

The c-GMP-PDE V inhibitory activity of representative compounds of the invention was demonstrated by the following procedure.

The cGMP-PDE and other PDE isozymes were isolated from cardiovascular tissues (heart and aorta) of various animal species and man by anion-exchange and affinity chromatography as described by Silver et al., Sec. Messeng. Phos. 13:13–25, 1991; PDE activity, in the presence and absence of test compounds was determined essentially as described by Thompson et al., Adv. Cyclic Nucleotide Res. 10:69–92. To determine the potency and selectivity of compounds as PDE inhibitors, compounds are screened for their effect on cyclic nucleotide hydrolysis at 10 µM. If ≧ 50% inhibition of PDE activity is observed, an IC$_{50}$ value (concentration of compound causing 50% reduction in PDE activity) and corresponding 95% confidence intervals are generated. The IC$_{50}$ values are calculated from concentration-response curves as described by Tallarida and Murray, Manual of Pharmacologic Calculations with Computer Programs, Procedure 8, Graded Dose-response, pp. 14–19, Springer-Verlag, New York, 1981.

The following table summarizes the results obtained from the testing of representative compounds of the invention.

| Example No. | Percent Inhibition at Given µM or IC$_{50}$ (nM) cGMP-PDE V |
|---|---|
| 1(c) | 83 |
| 2(c) | 82 |
| 3 | 300 |
| 4 | 3000 |
| 5 | 81% (10 µM) or 34% (1 µM) or 4% (0.1 µM) |
| 6(b) | 120 |
| 7(d) | 33 |
| 8 | 36 |
| 9(f) | 610 |
| 10(d) | 260 |
| 11(e) | 150 |
| 12 | 240 |
| 13 | 42 |
| 14 | 105 |
| 15(c) | 1.5 |
| 16(c) | 150 |
| 17(b) | 130 |
| 18(d) | 147 |
| 19(d) | 28% (0.1 µM) |
| 20 | 300 |
| 21 | 91 |
| 22 | 74 |
| 23(c) | 38 |
| 24(c) | 51 |
| 25 | 95% (10 µM) or 68% (1 µM) or 7% (0.1 µM) |
| 26 | 2.6/5.2* |
| 27 | 340/210/266* |
| 28(b) | 79% (10 µM) or 25% (1 µM) or 0% (0.1 µM) |
| 29(d) | 15 |
| 30 | 30 |
| 31 | 32 |
| 32 | 96% (10 µM) or 79% (1 µM) or 43% (0.1 µM) |
| 33 | 92 |
| 34 | 0.22/0.16/0.08* |
| 35 | 8.6/9.5/9.5* |
| 36(a) | 10.1 |
| 36(b) | 19.3 |
| 37(d) | 8.3/11.5* |
| 38 | 77% (1 µM) or 22% (0.1 µM) or 9% (0.01 µM) |
| 39 | 15 |
| 40(c) | 2.4 |
| 41(c) | 0.96 |
| 42(c) | 112 |
| 43 | 27 |
| 44(d) | 70% (1 µM) or 20% (0.1 µM) or 17% (0.01 µM) |
| 45(d) | 44 |
| 46 | 0.37 |
| 47(c) | 23 |
| 48(d) | 4.2 |
| 48(e) | 7.6 |
| 49 | 18 |

-continued

| Example No. | Percent Inhibition at Given μM or IC$_{50}$ (nM) cGMP-PDE V |
|---|---|
| 50 | 9.1 |
| 52 | 0.2/0.27* |
| 53(c) | 5.4 |
| 54 | 5.9/8.8* |
| 55 | 96% (0.1 μM) or 91% (0.01 μM) or 58% (0.001 μM) |

*The numbers represent IC$_{50}$ (nM) values for separate experimental runs.

The antihypertensive activity of representative compounds of the invention was demonstrated by the following procedure.

Spontaneously hypertensive rats (SHR) were anesthetized with sodium pentobarbital (50 mg/kg, ip) and instrumented with catheters positioned in the inferior vena cava and abdominal aorta for administration of drug and recording of arterial pressure and heart rate, respectively. After a 2 day recovery from surgery, three baseline blood pressure measurements were made at 5 min intervals in conscious SHR. Compounds to be tested or vehicle were then administered intravenously in a dose-dependent manner (0.3–10 mg base/kg) while arterial pressure was recorded continuously on a polygraph. The mean arterial pressure response was measured 5 minutes after the administration of each dose of the test compound and the next dose given in a cumulative dose fashion. The response to each dose of the test compound was calculated as the difference from the mean of the three baseline measurements.

The following table summarizes the results obtained from the testing of representative compounds of the invention.

| Example No. | SHR iv % change in mean arterial pressure at Given mg/kg or ED$_{25}$ (mg/kg) |
|---|---|
| 1(c) | −15% (10 mg/kg) |
| 6(b) | −23% (10 mg/kg) |
| 7(d) | −16% (3 mg/kg) |
| 8 | Inactive |
| 13 | −10% (1 mg/kg) |
| 15(c) | −18% (3 mg/kg) |
| 17(b) | −6% (10 mg/kg) |
| 21 | −12% (10 mg/kg) |
| 22 | −7% (10 mg/kg) |
| 23(c) | −7% (3 mg/kg) |
| 37(d) | −18% (10 mg/kg) or −15% (3 mg/kg) |

The activity of representative compounds of the invention in reversing or reducing nitrate-induced tolerance was demonstrated by the following procedure:

Spontaneously hypertensive rats (17–25 weeks of age) were made nitroglycerin tolerant by repeated administration of high doses of nitroglycerin (100 mg/kg, s.c., 3 times/day for 3 consecutive days). To confirm tolerance challenge doses of nitroglycerin were administered intravenously at doses ranging from 1–300 μg/kg and the maximum change in mean arterial pressure (MAP) for each dose was recorded. Groups of tolerant rats were pretreated with the compounds of the invention (tolerant pretreated group) or with vehicle (0.05 N NaOH) (tolerant vehicle pretreated group) intravenously 5–10 minutes prior to administration of challenge doses of nitroglycerin. The administration of challenge doses of nitroglycerin to non-tolerant rats (the non-tolerant group) caused a dose-dependent decrease in MAP of between 10 to 40 mm Hg. The administration of challenge doses of nitroglycerin to the tolerant vehicle pretreated group resulted in a significant reduction of the hypotensive response. The administration of challenge doses of nitroglycerin to tolerant rats which were pretreated with the compounds of the invention (tolerant pretreated group) resulted in varying degrees of restoration of the hypotensive response. The area under the dose-MAP curve was calculated for the non-tolerant group and for the tolerant vehicle pretreated group and the tolerant pretreated group. The percent reversal of nitrate-induced tolerance was calculated as follows:

Percent Reversal=$(AUC_{tol-pretreated}-AUC_{tol-veh})/(AUC_{nontol}-AUC_{tol-veh})\times 100$ wherein:

$AUC_{nontol}$ =the area under the dose-MAP curve for the non-tolerant group.

$AUC_{tol-veh}$=the area under the dose-MAP curve for the tolerant vehicle pretreated group.

$AUC_{tol-pretreated}$=the area under the dose-MAP curve for the tolerant pretreated group.

A percent reversal of 100% or greater reflects complete reversal of nitrate-induced tolerance, whereas a percent reversal of 0% indicates that no reversal of nitrate-induced tolerance occurred. The following table summarizes the results obtained from the testing of representative compounds of the invention.

| Example | Dose (mg/kg) | Percent (%) Reversal of Nitroglycerin-induced Tolerance |
|---|---|---|
| 34 | 1.0 | 44 |

The compounds of the invention can be prepared for pharmaceutical use by conventional pharmaceutical procedures that are well known in the art; that is, by formulating a pharmaceutical composition which comprises compounds of the invention or their pharmaceutically acceptable salts together with one or more physiologically acceptable carriers, adjuvants, diluents or vehicles, for oral administration in solid or liquid form, parenteral administration, topical administration or aerosol inhalation administration, and the like.

Solid compositions for oral administration include compressed tablets, pills, powders and granules. In such solid compositions, the active compound is admixed with at least one inert diluent such as starch, calcium carbonate, sucrose or lactose. These compositions may also contain additional substances other than inert diluents, e.g., lubricating agents, such as magnesium stearate, talc and the like.

Liquid compositions for oral administration include pharmaceutically acceptable emulsions, solutions, suspensions, syrups and elixirs containing inert diluents commonly used in the art, such as water and liquid paraffin. Besides inert diluents such compositions may also contain adjuvants, such as wetting and suspending agents, and sweetening, flavoring, perfuming and preserving agents. According to the invention, the compounds for oral administration also include capsules of absorbable material, such as gelatin, containing said active component with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. These compositions can also contain adjuvants such as stabilizing, preserving, wetting, emulsifying and dispersing agents.

Preparations according to the invention for topical administration or aerosol inhalation administration include dissolving or suspending a compound of the invention in a pharmaceutically acceptable vehicle such as water, aqueous alcohol, glycol, oil solution or oil-water emulsion, and the like.

If desired, the compounds of the invention can further be incorporated into slow release or targeted delivery systems such as polymer matrices, liposomes, and microspheres.

The percentage of active component in such compositions may be varied so that a suitable dosage is obtained. The dosage administered to a particular patient is variable depending upon the clinician's judgment using as criteria: The route of administration, the duration of treatment, the size and physical condition of the patient, the potency of the active component and the patient's response thereto. An effective dosage amount of the active component can thus readily be determined by the clinician after a consideration of all criteria and using his best judgment on the patient's behalf.

We claim:

1. A compound of the formula:

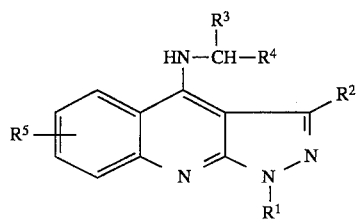

wherein:

$R^1$ is lower-alkyl, phenyl-lower-alkyl, or cycloalkyl;

$R^2$ is hydrogen, or lower-alkyl;

$R^3$ is hydrogen, lower-alkyl, or hydroxylower-alkyl;

$R^4$ is cycloalkyl or cylcoalkyl substituted by from one to two, the same or different, substituents selected from the group consisting of lower-alkoxycarbonyl, carboxy, lower-alkylthio-lower-alkoxycarbonyl, hydroxyloweralkyl, hydroxy, oxo, lower-alkoxy, lower-alkyl, and halogen; and $R^5$ is from one to three, the same or different, substituents selected from the group consisting of hydrogen, loweralkoxy, hydroxy, dilower-alkylamino-lower-alkoxy, carboxylower-alkoxy, lower-alkoxycarbonyl-loweralkoxy, nitro, polyhydroxylower-alkoxy, amino, epoxylower-alkoxy, carboxy, lower-alkanoylamino, loweralkoxycarbonyl, pyridinyl, 4-morpholinyl-loweralkoxy, lower-alkylsulfonyl, cyano, 1-imidazolyl, halogen, dilower-alkylaminosulfonyl, oxadiazolyl (or oxadiazolyl substituted on any available carbon atom thereof by lower-alkyl), lower-alkylsulfinyl, 1-pyrazolyl (or 1-pyrazolyl substituted on any available carbon atom thereof by lower-alkyl), trifluoromethylsulfonyl, lower-alkenyl, lower-alkyl, and lower-alkynyl; or a pharmaceutically acceptable acid-addition salt and/or hydrate and/or solvate thereof, or, where applicable, a stereoisomer or a racemic mixture thereof.

2. A compound according to claim 1 wherein $R^4$ is cycloalkyl or cylcoalkyl substituted by one substituent selected from the group consisting of lower-alkoxycarbonyl, lower-alkylthio-lower-alkoxycarbonyl, hydroxylower-alkyl, hydroxy, and oxo.

3. A compound according to claim 2 wherein $R^5$ is from one to two, the same or different, substituents selected from the group consisting of hydrogen, lower-alkoxy, hydroxy, dilower-alkylamino-lower-alkoxy, carboxylower-alkoxy, nitro, polyhydroxylower-alkoxy, amino, epoxyloweralkoxy, carboxy, lower-alkanoylamino, lower-alkoxycarbonyl, pyridinyl, 4-morpholinyl-lower-alkoxy, lower-alkylsulfonyl, cyano, 1-imidazolyl, halogen, diloweralkylaminosulfonyl, oxadiazolyl substituted on any available carbon atom thereof by lower-alkyl, lower-alkylsulfinyl, 1-pyrazolyl (or 1-pyrazolyl substituted on any available carbon atom thereof by lower-alkyl), trifluoromethylsulfonyl, and loweralkenyl.

4. A compound according to claim 3 wherein $R^1$ is ethyl, isopropyl, benzyl, or cyclopentyl; and $R^2$ is hydrogen, or methyl.

5. A compound according to claim 4 wherein $R^3$ is hydrogen, methyl, ethyl, or hydroxymethyl.

6. A compound according to claim 5 wherein $R^4$ is cycloalkyl selected from the group consisting of cyclohexyl, cyclopropyl, and adamantyl or said cycloalkyl group substituted by one substituent selected from the group consisting of methoxycarbonyl, methylthiomethoxycarbonyl, hydroxymethyl, hydroxy, and oxo.

7. A compound according to claim 6 wherein $R^5$ is from one to two, the same or different, substituents selected from the group consisting of hydrogen, methoxy, hydroxy, 2-(dimethylamino)ethoxy, carboxymethoxy, nitro, 2,3-dihydroxypropoxy, amino, 2,3-epoxypropoxy, 1-carboxyethoxy, carboxy, acetylamino, methoxycarbonyl, pyridinyl, 2-(4-morpholinyl) ethoxy, methylsulfonyl, cyano, 1-imidazolyl, bromo, diethylaminosulfonyl, 5-methyl-3-(1,2,4-oxadiazolyl), methylsulfinyl, 4-methyl-1-pyrazolyl, 1-pyrazolyl, trifluoromethylsulfonyl, and ethenyl.

8. A compound according to claim 7 selected from the group consisting of:

1-ethyl-6-nitro-N-[S(+)-1-(cyclohexyl) ethyl]-1H-pyrazolo [3,4-b]quinolin-4-amine, 1-ethyl -6-nitro-N-[cyclohexylmethyl]- 1H-pyrazolo [3,4-b]quinolin-4-amine, 1-ethyl-6-cyano-N-[S(+)-1-(cyclohexyl)ethyl]-1H-pyrazolo [3,4-b]quinolin-4-amine, 1-ethyl-6-bromo-N-[S(+)-1-(cyclohexyl)ethyl]-1H-pyrazolo [3,4-b]quinolin-4-amine, and 1-ethyl-6-(1-pyrazolyl)-N-[S(+)-1-(cyclohexyl)ethyl]-1H-pyrazolo [3,4-b]quinolin-4-amine.

9. 1 -Ethyl -6-nitro-N-[S (+)-1-(cyclohexyl)ethyl]-1H-pyrazolo [3,4-b]quinolin-4-amine according to claim 8.

10. A pharmaceutical composition which comprises a compound according to claim 1 together with a pharmaceutically acceptable carrier, adjuvant, diluent, or vehicle.

11. A pharmaceutical composition which comprises a compound according to claim 2 together with a pharmaceutically acceptable carrier, adjuvant, diluent, or vehicle.

12. A pharmaceutical composition which comprises a compound according to claim 3 together with a pharmaceutically acceptable carrier, adjuvant, diluent, or vehicle.

13. A pharmaceutical composition which comprises a compound according to claim 4 together with a pharmaceutically acceptable carrier, adjuvant, diluent, or vehicle.

14. A pharmaceutical composition which comprises a compound according to claim 5 together with a pharmaceutically acceptable carrier, adjuvant, diluent, or vehicle.

15. A pharmaceutical composition which comprises a compound according to claim 6 together with a pharmaceutically acceptable carrier, adjuvant, diluent, or vehicle.

16. A pharmaceutical composition which comprises a compound according to claim 7 together with a pharmaceutically acceptable carrier, adjuvant, diluent, or vehicle.

17. A pharmaceutical composition which comprises a compound according to claim 8 together with a pharmaceutically acceptable carrier, adjuvant, diluent, or vehicle.

18. A pharmaceutical composition which comprises a compound according to claim 9 together with a pharmaceutically acceptable carrier, adjuvant, diluent, or vehicle.

19. A method for effecting cGMP-phosphodiesterase inhibition in a mammalian organism which comprises administering to said organism an effective amount of a compound according to claim 1.

20. A method for effecting cGMP-phosphodiesterase inhibition in a mammalian organism which comprises administering to said organism an effective amount of a compound according to claim 2.

21. A method for effecting cGMP-phosphodiesterase inhibition in a mammalian organism which comprises administering to said organism an effective amount of a compound according to claim 3.

22. A method for effecting cGMP-phosphodiesterase inhibition in a mammalian organism which comprises administering to said organism an effective amount of a compound according to claim 4.

23. A method for effecting cGMP-phosphodiesterase inhibition in a mammalian organism which comprises administering to said organism an effective amount of a compound according to claim 5.

24. A method for effecting cGMP-phosphodiesterase inhibition in a mammalian organism which comprises administering to said organism an effective amount of a compound according to claim 6.

25. A method for effecting cGMP-phosphodiesterase inhibition in a mammalian organism which comprises administering to said organism an effective amount of a compound according to claim 7.

26. A method for effecting cGMP-phosphodiesterase inhibition in a mammalian organism which comprises administering to said organism an effective amount of a compound according to claim 8.

27. A method for effecting cGMP-phosphodiesterase inhibition in a mammalian organism which comprises administering to said organism an effective amount of a compound according to claim 9.

28. A method of treating heart failure and/or hypertension in a mammalian organism which comprises administering to said organism an effective amount of a compound according to claim 1.

29. A method of treating heart failure and/or hypertension in a mammalian organism which comprises administering to said organism an effective amount of a compound according to claim 2.

30. A method of treating heart failure and/or hypertension in a mammalian organism which comprises administering to said organism an effective amount of a compound according to claim 3.

31. A method of treating heart failure and/or hypertension in a mammalian organism which comprises administering to said organism an effective amount of a compound according to claim 4.

32. A method of treating heart failure and/or hypertension in a mammalian organism which comprises administering to said organism an effective amount of a compound according to claim 5.

33. A method of treating heart failure and/or hypertension in a mammalian organism which comprises administering to said organism an effective amount of a compound according to claim 6.

34. A method of treating heart failure and/or hypertension in a mammalian organism which comprises administering to said organism an effective amount of a compound according to claim 7.

35. A method of treating heart failure and/or hypertension in a mammalian organism which comprises administering to said organism an effective amount of a compound according to claim 8.

36. A method of treating heart failure and/or hypertension in a mammalian organism which comprises administering to said organism an effective amount of a compound according to claim 9.

37. A method for reversing or reducing nitrate-induced tolerance in a mammalian organism undergoing nitrate therapy which comprises administering to said organism an effective amount of a compound according to claim 1.

38. A method for reversing or reducing nitrate-induced tolerance in a mammalian organism undergoing nitrate therapy which comprises administering to said organism an effective amount of a compound according to claim 2.

39. A method for reversing or reducing nitrate-induced tolerance in a mammalian organism undergoing nitrate therapy which comprises administering to said organism an effective amount of a compound according to claim 3.

40. A method for reversing or reducing nitrate-induced tolerance in a mammalian organism undergoing nitrate therapy which comprises administering to said organism an effective amount of a compound according to claim 4.

41. A method for reversing or reducing nitrate-induced tolerance in a mammalian organism undergoing nitrate therapy which comprises administering to said organism an effective amount of a compound according to claim 5.

42. A method for reversing or reducing nitrate-induced tolerance in a mammalian organism undergoing nitrate therapy which comprises administering to said organism an effective amount of a compound according to claim 6.

43. A method for reversing or reducing nitrate-induced tolerance in a mammalian organism undergoing nitrate therapy which comprises administering to said organism an effective amount of a compound according to claim 7.

44. A method for reversing or reducing nitrate-induced tolerance in a mammalian organism undergoing nitrate therapy which comprises administering to said organism an effective amount of a compound according to claim 8.

45. A method for reversing or reducing nitrate-induced tolerance in a mammalian organism undergoing nitrate therapy which comprises administering to said organism an effective amount of a compound according to claim 9.

46. A method for treating angina pectoris, congestive heart disease and myocardial infarction in a mammalian organism which comprises administering to said organism an effective amount of a compound according to claim 1 in combination with a nitrate.

47. A method for treating angina pectoris, congestive heart disease and myocardial infarction in a mammalian organism which comprises administering to said organism an effective amount of a compound according to claim 2 in combination with a nitrate.

48. A method for treating angina pectoris, congestive heart disease and myocardial infarction in a mammalian organism which comprises administering to said organism an effective amount of a compound according to claim 3 in combination with a nitrate.

49. A method for treating angina pectoris, congestive heart disease and myocardial infarction in a mammalian organism which comprises administering to said organism an effective amount of a compound according to claim 4 in combination with a nitrate.

50. A method for treating angina pectoris, congestive heart disease and myocardial infarction in a mammalian organism which comprises administering to said organism an effective amount of a compound according to claim 5 in combination with a nitrate.

51. A method for treating angina pectoris, congestive heart disease and myocardial infarction in a mammalian organism which comprises administering to said organism an effective amount of a compound according to claim 6 in combination with a nitrate.

52. A method for treating angina pectoris, congestive heart disease and myocardial infarction in a mammalian organism which comprises administering to said organism an effective amount of a compound according to claim 7 in combination with a nitrate.

53. A method for treating angina pectoris, congestive heart disease and myocardial infarction in a mammalian organism which comprises administering to said organism an effective amount of a compound according to claim 8 in combination with a nitrate.

54. A method for treating angina pectoris, congestive heart disease and myocardial infarction in a mammalian organism which comprises administering to said organism an effective amount of a compound according to claim 9 in combination with a nitrate.

* * * * *